US012686678B2

(12) United States Patent
Chen et al.

(10) Patent No.: US 12,686,678 B2
(45) Date of Patent: Jul. 21, 2026

(54) CRYSTAL FORM OF LANIFIBRANOR, PREPARATION METHOD THEREFOR, AND USE THEREOF

(71) Applicant: INVENTIVA, Daix (FR)

(72) Inventors: Minhua Chen, Suzhou (CN); Hongyan Zhu, Suzhou (CN)

(73) Assignee: INVENTIVA, Daix (FR)

( * ) Notice: Subject to any disclaimer, the term of this patent is extended or adjusted under 35 U.S.C. 154(b) by 418 days.

(21) Appl. No.: 18/518,719

(22) Filed: Nov. 24, 2023

(65) Prior Publication Data

US 2024/0092771 A1 Mar. 21, 2024

Related U.S. Application Data

(60) Division of application No. 17/887,681, filed on Aug. 15, 2022, now Pat. No. 11,827,630, which is a continuation of application No. PCT/CN2021/137078, filed on Dec. 10, 2021.

(30) Foreign Application Priority Data

| | | |
|---|---|---|
| Dec. 11, 2020 | (CN) | 202011460164.4 |
| Dec. 11, 2020 | (CN) | 202011463478.X |
| Jul. 8, 2021 | (CN) | 202110771569.8 |

(51) Int. Cl.
*C07D 417/12* (2006.01)
*A61P 1/16* (2006.01)

(52) U.S. Cl.
CPC .............. *C07D 417/12* (2013.01); *A61P 1/16* (2018.01); *C07B 2200/13* (2013.01)

(58) Field of Classification Search
CPC .................................................... C07D 417/12
See application file for complete search history.

(56) References Cited

FOREIGN PATENT DOCUMENTS

| | | | |
|---|---|---|---|
| CN | 101248044 | A | 8/2008 |
| CN | 109316601 | A | 2/2019 |
| IN | 201911052572 | A | 9/2021 |
| WO | 2007026097 | A1 | 3/2007 |
| WO | 2015189401 | A1 | 12/2015 |
| WO | 2019024776 | A1 | 2/2019 |
| WO | 2022106412 | A1 | 5/2022 |

OTHER PUBLICATIONS

International Application No. PCT/CN2021/137078, International Search Report and Written Opinion mailed Mar. 9, 2022, 11 pages.

Benaissa et al., "Design, Synthesis, and Evaluation of a Novel Series of Indole Sulfonamide Peroxisome Proliferator Activated Receptor (PPAR)α/γ/δ Triple Activators: Discovery of Lanifibranor, a New Antifibrotic Clinical Candidate," Journal of Medicinal Chemistry,vol. 61, Feb. 15, 2018, pp. 2246-2265.

Maghsoodi et al. "Role of solvent in improvement of dissolution rate of drugs: crystal habit and crystal agglomeration," Adv Pharm Bui. 2015, 5(1) pp. 13-18 (Year: 2015).

Inventiva Study Protocol, 5.1, Mar. 25, 2020 https://clinicaltrials.gov/ProvidedDocs/70/NCT03008070/Prot_001.pdf (Year: 2020).

Pace et al. "2-methyltetrahydrofuran (2-MeTHF): A biomass-derived solvent with broad application in Organic Chemistry," ChemSusChem 2012, 5, 1369-1379 (Year: 2012).

*Primary Examiner* — John S Kenyon
(74) *Attorney, Agent, or Firm* — COOLEY LLP

(57) ABSTRACT

Provided are novel crystalline forms of Lanifibranor (Referred to as "Compound I") and preparation methods thereof, pharmaceutical compositions containing the crystalline forms, and uses of the crystalline forms for preparing pan-PPAR agonists drugs and drugs for treating NASH. Compared with prior arts, the provided crystalline forms of Compound I have one or more improved properties, which solve the problems of the prior art and is of great value to the optimization and development of the drugs.

Compound I

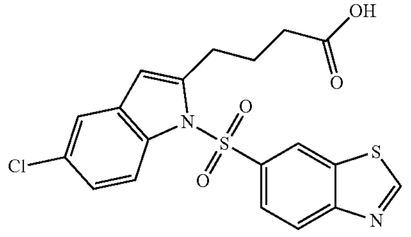

12 Claims, 25 Drawing Sheets

CRYSTAL FORM OF LANIFIBRANOR, PREPARATION METHOD THEREFOR, AND USE THEREOF

This is a divisional application of U.S. application Ser. No. 17/887,681 filed on Aug. 15, 2022, which is a continuation application of international application No. PCT/CN2021/13078 filed on Dec. 10, 2021, which claims priority from Chinese patent application Nos. CN202011463478.X, CN202011460164.4 and CN202110771569.8, filed on Dec. 11, 2020, Dec. 11, 2020 and Jul. 8, 2021, respectively. The content of U.S. application Ser. No. 17/887,681, Chinese patent application Nos. CN202011463478.X, CN202011460164.4, and CN202110771569.8 is incorporated herein by reference in their entirety.

TECHNICAL FIELD

The present disclosure pertains to the field of chemical crystallography, particularly relates to novel crystalline forms of Lanifibranor, preparation method and use thereof.

BACKGROUND

Non-alcoholic steatohepatitis (NASH) is a severe liver disease with steatosis accompanied by inflammation and hepatocellular injury.

Peroxisome proliferator-activated receptor (PPAR) are ligand-activated transcription factors belonging to the nuclear hormone receptor family that regulate the expression of target genes. PPAR play essential roles in the regulation of cellular differentiation, development, and tumorigenesis.

Lanifibranor is an orally-available small molecule that acts to induce anti-fibrotic, anti-inflammatory by activating each of the three PPAR isoforms, known as PPARα, PPARδ and PPARγ. lanifibranor can addresses steatosis by enhancing fatty acid metabolism and ultimately decreasing lipogenesis.

The chemical name of Lanifibranor is 5-Chloro-1-[(6-benzothiazolyl)sulfonyl]-1H-indole-2-butanoic acid (Referred to as Compound I), and the structure is shown as the follows:

Compound I

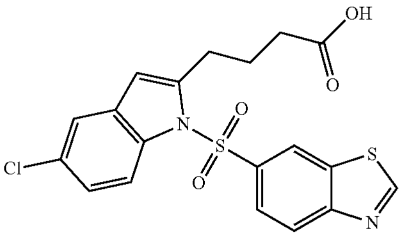

A crystalline form is a solid material whose constituents are arranged in a highly ordered microscopic structure, forming a crystal lattice that extends in all directions. Polymorphism refers to the phenomenon that a compound exists in more than one crystalline form. Compounds may exist in one or more crystalline forms, but their existence and characteristics cannot be predicted with any certainty. Different crystalline forms of drug substances have different physicochemical properties, which can affect drug's in vivo dissolution and absorption and will further affect drug's clinical efficacy and safety to some extent. In particular, for some poorly soluble oral solid or semi-solid dosage forms, crystalline forms can be crucial to the performance of drug product. In addition, the physiochemical properties of a crystalline form are very important to the manufacturing process. Therefore, polymorphism is an important part of drug research and drug quality control.

Amorphous forms are non-crystalline materials which possess no long-range order. Typically, an amorphous form will exhibit a broad "halo" XRPD pattern.

Example 117 of prior art WO2007026097A1 disclosed the preparation of Compound I as: "the white precipitate is extracted with ethyl acetate and the organic phase is separated off, dried over magnesium sulfate and concentrated under reduced pressure to give Compound I in the form of a pale yellow powder (yield=83%)." Example 3 of prior art WO2019024776A1 disclosed the preparation of Compound I as: "the white precipitate is extracted with ethyl acetate and the organic phase is separated off, dried over magnesium sulfate and concentrated under reduced pressure to give 83 mg pale yellow solid of Compound I." The inventors of the present disclosure repeated the preparation method of Compound I disclosed in prior arts and obtained the amorphous of Compound I. The inventors of the present disclosure have systematically evaluated the properties of the amorphous obtained according to the prior arts. The results show that the amorphous has the problems of poor hygroscopicity, high organic solvent residue, poor powder condition, difficulty of quantification and large weight loss during transfer and is not suitable for pharmaceutical use.

In order to overcome the disadvantages of prior arts, a new crystalline form meeting the medicinal standard is still needed for the development of drugs containing Compound I. The inventors of the present disclosure surprisingly obtained 1,4-dioxane solvate, chloroform solvate, tetrahydrofuran solvate, anhydrous and hydrate of Compound I. Among them, 1,4-dioxane solvate, trichloromethane solvate and tetrahydrofuran solvate contain 10.1 wt % of 1,4-dioxane, 3.3 wt % of trichloromethane and 6.0 wt % of tetrahydrofuran and are not suitable for pharmaceutical use. The anhydrate and hydrate of Compound I provided by the present disclosure have advantages in at least one aspect of solubility, hygroscopicity, purification ability, stability, adhesiveness, compressibility, flowability, in vitro and in vivo dissolution, and bioavailability, etc. In particular, the crystalline forms of the Compound I of the present disclosure have advantages such as good stability, good hygroscopicity, no solvent residue, uniform particle size distribution, good flowability, low adhesiveness, good dispersion of crystalline powder, which solves the problems existing in the prior arts and are of great significance for the development of drugs containing Compound I.

SUMMARY OF THE INVENTION

The present disclosure is to provide novel crystalline forms of Compound I, preparation method and pharmaceutical compositions comprising the crystalline forms.

Furthermore, a hydrate of Compound I is provided by the present disclosure.

Furthermore, an anhydrate of Compound I is provided by the present disclosure.

Furthermore, the crystalline forms of Compound I provided by the present disclosure have no greater than 5 wt % water content.

Furthermore, the crystalline forms of Compound I provided by the present disclosure have no greater than 3 wt % water content.

Furthermore, crystalline form CSI of Compound I is provided by the present disclosure (hereinafter referred to as Form CSI).

In one aspect provided herein, the X-ray powder diffraction pattern of Form CSI comprises one or two or three characteristic peaks at 2theta values of 20.2°±0.2°, 22.2°±0.2°, and 24.5°±0.2° using CuKα radiation. Preferably, the X-ray powder diffraction pattern of Form CSI comprises characteristic peaks at 2theta values of 20.2°±0.2°, 22.2°±0.2°, and 24.5°±0.2° using CuKα radiation.

Furthermore, the X-ray powder diffraction pattern of Form CSI comprises one or two or three characteristic peaks at 2theta values of 7.7°±0.2°, 17.8°±0.2°, and 21.2°±0.2° using CuKα radiation. Preferably, the X-ray powder diffraction pattern of Form CSI comprises characteristic peaks at 2theta values of 7.7°±0.2°, 17.8°±0.2°, and 21.2°±0.2° using CuKα radiation.

Furthermore, the X-ray powder diffraction pattern of Form CSI comprises one or two or three characteristic peaks at 2theta values of 10.9°±0.2°, 16.4°±0.2°, and 19.1°±0.2° using CuKα radiation. Preferably, the X-ray powder diffraction pattern of Form CSI comprises characteristic peaks at 2theta values of 10.9°±0.2°, 16.4°±0.2°, and 19.1°±0.2° using CuKα radiation.

In another aspect provided herein, the X-ray powder diffraction pattern of Form CSI comprises one or two or three or four or five or six or seven or eight or nine or ten or eleven or twelve or thirteen characteristic peaks at 2theta values of 20.2°±0.2°, 22.2°±0.2°, 24.5°±0.2°, 7.7°±0.2°, 17.8°±0.2°, 21.2°±0.2°, 10.9°±0.2°, 16.4°±0.2°, 19.1°±0.2°, 25.3°±0.2°, 14.0°±0.2°, 15.6°±0.2°, and 17.0°±0.2° using CuKα radiation.

Without any limitation being implied, the X-ray powder diffraction pattern of Form CSI is substantially as depicted in FIG. 1.

Without any limitation being implied, the Thermo Gravimetric Analysis (TGA) curve of Form CSI is substantially as depicted in FIG. 2, which shows 0.02% weight loss when heated to 170° C.

Without any limitation being implied, Form CSI is an anhydrate.

Without any limitation being implied, the single crystal structure parameters of Form CSI are shown in Table 1.

TABLE 1

| | |
|---|---|
| Empirical formula | $C_{19}H_{15}ClN_2O_4S_2$ |
| Formula weight | 434.90 |
| Temperature | 293(2) K |
| X-Ray source | Cu/Kα (λ = 1.54184 Å) |
| Crystal system | monoclinic |
| Space group | $P2_1/n$ |
| Unit cell dimensions | a = 14.8715(9) Å |
| | b = 7.8511(6) Å |
| | c = 16.2886(8) Å |
| | α = 90° |
| | β = 94.332(5)° |
| | γ = 90° |
| Volume | 1896.4(2) $Å^3$ |
| Number of molecules per unit cell (Z) | 4 |
| Calculated density | 1.523 $g/cm^3$ |

According to the objective of the present disclosure, a process for preparing Form CSI is also provided. The process comprises:

method 1: adding Compound I in an alcohol or an ether, stirring and separating to obtain Form CSI; or method 2: dissolving Compound I into an ether or hydrocarbon to form a clear solution, evaporating the clear solution to obtain Form CSI.

Furthermore, in method 1, said alcohol is preferably a C1-C8 alcohol, further preferably methanol; said ether is preferably a C4-C7 ether, further preferably methyl tert-butyl ether; said stirring time is preferably at least 10 minutes.

Furthermore, in method 2, said ether is preferably a C4-C7 ether, further preferably 2-methyltetrahydrofuran; said hydrocarbon is preferably a C5-C8 hydrocarbon, further preferably aromatic hydrocarbon, further preferably methylbenzene.

According to the objective of the present disclosure, crystalline form CSII of Compound I is provided (hereinafter referred to as Form CSII).

In one aspect provided herein, the X-ray powder diffraction pattern of Form CSII comprises one or two or three characteristic peaks at 2theta values of 18.4°±0.2°, 22.4°±0.2°, and 25.3°±0.2° using CuKα radiation. Preferably, the X-ray powder diffraction pattern of Form CSII comprises characteristic peaks at 2theta values of 18.4°±0.2°, 22.4°±0.2°, and 25.3°±0.2° using CuKα radiation.

Furthermore, the X-ray powder diffraction pattern of Form CSII comprises one or two or three characteristic peaks at 2theta values of 7.9°±0.2°, 13.2°±0.2°, and 20.6°±0.2° using CuKα radiation. Preferably, the X-ray powder diffraction pattern of Form CSII comprises characteristic peaks at 2theta values of 7.9°±0.2°, 13.2°±0.2°, and 20.6°±0.2° using CuKα radiation.

Furthermore, the X-ray powder diffraction pattern of Form CSII comprises one or two or three characteristic peaks at 2theta values of 9.7°±0.2°, 23.1°±0.2°, and 24.2°±0.2° using CuKα radiation. Preferably, the X-ray powder diffraction pattern of Form CSII comprises characteristic peaks at 2theta values of 9.7°±0.2°, 23.1°±0.2°, and 24.2°±0.2° using CuKα radiation.

In another aspect provided herein, the X-ray powder diffraction pattern of Form CSII comprises one or two or three or four or five or six or seven or eight or nine or ten or eleven or twelve characteristic peaks at 2theta values of 18.4°±0.2°, 22.4°±0.2°, 25.3°±0.2°, 7.9°±0.2°, 13.2°±0.2°, 20.6°±0.2°, 9.7°±0.2°, 23.1°±0.2°, 24.2°±0.2°, 26.3°±0.2°, 14.4°±0.2°, and 16.8°±0.2° using CuKα radiation.

In another aspect provided herein, the X-ray powder diffraction pattern of Form CSII comprises one or two or three or four or five or six or seven or eight or nine or ten or eleven or twelve characteristic peaks at 2theta values of 18.5°±0.2°, 22.4°±0.2°, 25.5°±0.2°, 7.9°±0.2°, 13.2°±0.2°, 20.7°±0.2°, 9.8°±0.2°, 23.2°±0.2°, 24.2°±0.2°, 26.4°±0.2°, 14.4°±0.2°, and 16.9°±0.2° using CuKα radiation.

Without any limitation being implied, the X-ray powder diffraction pattern of Form CSII is substantially as depicted in FIG. 5.

Without any limitation being implied, the TGA curve of Form CSII is substantially as depicted in FIG. 6, which shows 2.2% weight loss when heated to 180° C.

Without any limitation being implied, the Differential Scanning calorimetry (DSC) curve of Form CSII is substantially as depicted in FIG. 7, which shows an endothermic peak at around 143° C., an exothermic peak at around 151° C., an endothermic peak at around 177° C. (onset temperature).

Without any limitation being implied, Form CSII is a hydrate.

According to the objective of the present disclosure, a process for preparing Form CSII is also provided. The process comprises:

adding Compound I in a solvent to form a clear solution and volatilizing the clear solution to obtain Form CSII, wherein the solvent is selected from an alcohol, a ketone, a solvent mixture of ether and nitrile.

Furthermore, said alcohol is preferably a C1-C8 alcohol, said ketone is preferably a C3-C6 ketone, said ether is preferably a C4-C7 ether, said nitrile is preferably C2-C4 nitrile.

Furthermore, said alcohol is preferably methanol and/or n-propanol, said ketone is preferably methyl ethyl ketone, said ether is preferably tetrahydrofuran, said nitrile is preferably acetonitrile.

Furthermore, the volume ratio of ether and nitrile in the said mixture solvent is preferably 10:1-1:10.

According to the objective of the present disclosure, crystalline form CSIV of Compound I is provided (hereinafter referred to as Form CSIV).

In one aspect provided herein, the X-ray powder diffraction pattern of Form CSIV comprises characteristic peaks at 2theta values of 11.4°±0.2°, 24.7°±0.2°, and 25.8°±0.2° using CuKα radiation.

Furthermore, the X-ray powder diffraction pattern of Form CSIV comprises one or two or three characteristic peaks at 2theta values of 15.3°±0.2°, 20.1°±0.2°, and 27.6°±0.2° using CuKα radiation. Preferably, the X-ray powder diffraction pattern of Form CSIV comprises characteristic peaks at 2theta values of 15.3°±0.2°, 20.1°±0.2°, and 27.6°±0.2° using CuKα radiation.

Furthermore, the X-ray powder diffraction pattern of Form CSIV comprises one or two or three characteristic peaks at 2theta values of 8.9°±0.2°, 15.9°±0.2°, and 20.9°±0.2° using CuKα radiation. Preferably, the X-ray powder diffraction pattern of Form CSIV comprises characteristic peaks at 2theta values of 8.9°±0.2°, 15.9°±0.2°, and 20.9°±0.2° using CuKα radiation.

In another aspect provided herein, the X-ray powder diffraction pattern of Form CSIV comprises one or two or three or four or five or six or seven or eight or nine or ten or eleven or twelve or thirteen or fourteen or fifteen characteristic peaks at 2theta values of 11.4°±0.2°, 24.7°±0.2°, 25.8°±0.2°, 15.3°±0.2°, 20.1°±0.2°, 27.6°±0.2°, 8.9°±0.2°, 15.9°±0.2°, 20.9°±0.2°, 7.3°±0.2°, 9.4°±0.2°, 11.7°±0.2°, 17.8°±0.2°, 18.8°±0.2°, and 24.3°±0.2° using CuKα radiation.

Without any limitation being implied, the X-ray powder diffraction pattern of Form CSIV is substantially as depicted in FIG. 9.

Without any limitation being implied, the TGA curve of Form CSIV is substantially as depicted in FIG. 10, which shows 0.06% weight loss when heated to 120° C.

Without any limitation being implied, Form CSIV is an anhydrate.

According to the objective of the present disclosure, a process for preparing Form CSIV is also provided. The process comprises:

heating Compound I solid to 180° C.-200° C., cooling to room temperature, heating the obtained solid to a certain temperature again, and then cooling to room temperature to obtain Form CSIV.

Furthermore, said a certain temperature is preferably 120° C.-160° C.

According to the objective of the present disclosure, the present disclosure also provides the use of Form CSI, Form CSII or Form CSIV or combinations thereof for preparing other crystalline forms, or salts of Compound I.

According to the objective of the present disclosure, a pharmaceutical composition is provided, said pharmaceutical composition comprises a therapeutically effective amount of crystalline form of Compound I and pharmaceutically acceptable excipients.

Furthermore, a pharmaceutical composition is provided, said pharmaceutical composition comprises a therapeutically effective amount of Form CSI, Form CSII or Form CSIV or combinations thereof and pharmaceutically acceptable excipients.

According to the objective of the present disclosure, crystalline forms of Compound I can be used for preparing pan-PPAR agonist drugs.

Furthermore, Form CSI, Form CSII or Form CSIV or combinations thereof can be used for preparing pan-PPAR agonist drugs.

According to the objective of the present disclosure, crystalline forms of Compound I can be used for preparing drugs treating NASH.

Furthermore, Form CSI, Form CSII or Form CSIV or combinations thereof can be used for preparing drugs treating NASH.

Technical Problems Solved by the Present Disclosure

The inventors of the present disclosure have systematically evaluated the properties of the amorphous obtained according to the prior arts and the results show that the amorphous has poor hygroscopicity and poor chemical stability, which is not conducive to production. Meanwhile, the amount of organic solvent residues in the amorphous is far beyond the solvent residue limit of the Pharmacopoeia, and the toxicity is high. In order to solve the problems existing in the prior arts, the inventors of the present disclosure have conducted more than 600 experiments with different methods, such as slurry, volatilization, liquid vapor diffusion, solid vapor diffusion, humidity induction, anti-solvent addition and heating in different solvent systems, and finally unexpectedly obtained crystalline forms of Compound I provided by the present disclosure.

Technical Effects

Form CSI of the present disclosure has the following advantages:

(1) Compared with prior arts, Form CSI of the present disclosure has better hygroscopicity. The test results show that the weight gains of prior art amorphous from 0 to 60% relative humidity (RH) and from 0 to 70% RH are about 6 times and 7 times that of Form CSI. The weight gains of Form CSI from 0 to 60% RH and from 0 to 70% RH are both 0.17%, the weight gains of prior art amorphous from 0 to 60% RH and from 0 to 70% RH are 0.94% and 1.18%, respectively.

In one aspect, poor hygroscopicity tends to cause chemical degradation and polymorph transformation, which directly affects the physicochemical stability of the drug substance. In addition, poor hygroscopicity will reduce the flowability of the drug substance, thereby affecting the processing of the drug substance.

In another aspect, drug substance with poor hygroscopicity requires low humidity environment during production and storage, which puts strict requirements on production and imposes higher costs. More importantly, poor hygroscopicity is likely to cause variation in the content of active pharmaceutical ingredients in the drug product, thus affecting drug product quality.

Form CSI provided by the present disclosure with good hygroscopicity is not demanding on the production and storage conditions, which reduces the cost of production, storage and quality control, and has strong economic value.

(2) Form CSI provided by the present disclosure has good appearance. Form CSI has good powder dispersibility, which is beneficial to transfer and reduce weight loss in industrial production.

(3) From CSI drug substance of the present disclosure has good stability. Crystalline state of Form CSI drug substance doesn't change for at least 6 months when stored under the condition of 25° C./60% RH with open and sealed package. The chemical purity remains substantially unchanged during storage. The results show that From CSI drug substance has good stability under long term condition, which is beneficial to the drug storage.

Meanwhile, crystalline state of Form CSI drug substance doesn't change for at least 6 months when stored under the condition of 40° C./75% RH with open and sealed package, and the chemical purity remains substantially unchanged during storage. The crystalline form of Form CSI drug substance doesn't change for at least 3 months when stored under the condition of 60° C./75% RH with open and sealed package, and the chemical purity remains substantially unchanged during storage. These results show that Form CSI drug substance has good stability under accelerated and stress conditions. Drug substance would go through high temperature and high humidity conditions caused by different season, regional climate and environment during storage, transportation, and manufacturing processes. Therefore, good stability under accelerated and stress conditions is of great importance to the drug development. Form CSI drug substance has good stability under stress condition, which is beneficial to avoid the impact on drug quality due to crystal transformation or decrease in purity during drug storage.

(4) Form CSI of the present disclosure has uniform particle size distribution. Uniform particle size helps to ensure uniformity of content and reduce variability of in vitro dissolution.

(5) Form CSI of the present disclosure has better flowability. Better flowability can prevent clogging of production equipment and increase manufacturing efficiency. Better flowability of Form CSI ensures the content uniformity of the drug product, reduces the weight variation of the drug product and improves product quality.

(6) Form CSI of the present disclosure shows low adhesiveness. Low adhesiveness can reduce the agglomeration of drug substance and effectively improve the adhesion to roller and tooling during dry-granulation and compression process. It is conducive to the dispersion of drug substance with excipients and improving the blend uniformity of the mixing of materials, which ultimately improves product quality.

Form CSII of the present disclosure has the following advantages:

(1) Compared with prior arts, Form CSII of the present disclosure has better hygroscopicity. The test results show that the weight gains of prior art amorphous from 0 to 60% RH and from 0 to 70% RH are about 4 times and 5 times that of Form CSII. The weight gains of Form CSII from 0 to 60% RH and from 0 to 70% RH are 0.21% and 0.27%, the weight gains of prior art amorphous from 0 to 60% RH and from 0 to 70% RH are 0.94% and 1.18%, respectively.

In one aspect, poor hygroscopicity tends to cause chemical degradation and polymorph transformation, which directly affects the physicochemical stability of the drug substance. In addition, poor hygroscopicity will reduce the flowability of the drug substance, thereby affecting the processing of the drug substance.

In another aspect, drug substance with poor hygroscopicity requires low humidity environment during production and storage, which puts strict requirements on production and imposes higher costs. More importantly, poor hygroscopicity is likely to cause variation in the content of active pharmaceutical ingredients in the drug product, thus affecting drug product quality.

Form CSII provided by the present disclosure with better hygroscopicity is not demanding on the production and storage conditions, which reduces the cost of production, storage and quality control, and has strong economic value.

(2) Form CSII provided by the present disclosure has good appearance. Form CSII has good powder dispersibility, which is beneficial to transfer and reduce material weight loss in industrial production.

(3) From CSII drug substance of the present disclosure has good stability. Crystalline state of Form CSII drug substance doesn't change for at least 3 months when stored under the condition of 25° C./60% RH with open and sealed packaged. The chemical purity remains substantially unchanged during storage. The results show that From CSII drug substance has good stability under long term condition, which is beneficial to the drug storage.

Meanwhile, crystalline state of Form CSII drug substance doesn't change for at least 3 months when stored under the condition of 40° C./75% RH with open and sealed package, and the chemical purity remains substantially unchanged during storage. The crystalline form of Form CSII drug substance doesn't change for at least one month when stored under the condition of 60° C./75% RH with open package, and the chemical purity remains substantially unchanged during storage. These results show that Form CSII drug substance has good stability under accelerated and stress conditions. Drug substance would go through high temperature and high humidity conditions caused by different season, regional climate and environment during storage, transportation, and manufacturing processes. Therefore, good stability under accelerated and stress conditions is of great importance to the drug development. Form CSII drug substance has good stability under stress condition, which is beneficial to avoid the impact on drug quality due to crystal transformation or decrease in purity during drug storage.

Meanwhile, Form CSII has good physical stability under mechanical force. Form CSII drug substance has good physical stability after tableting and grinding. Grinding and pulverization are often required in the drug manufacturing process. Good physical stability of the drug substance can reduce the risk of crystallinity decrease and crystal transformation during the drug production process. Form CSII has good physical stability under different pressures, which is beneficial to keep crystalline form unchanged during tableting process.

(4) Form CSII of the present disclosure shows low adhesiveness. Low adhesiveness can reduce the agglomeration of drug substance and effectively improve the adhesion to roller and tooling during dry-granulation and compression process. It is conducive to the dispersion of drug substance with excipients and improving the blend uniformity of the mixing of materials, which ultimately improves product quality.

Form CSIV of the present disclosure has the following advantages:

(1) Compared with prior arts, Form CSIV of the present disclosure has better hygroscopicity. The test results show that the weight gains of amorphous from 0 to 60% RH and from 0 to 70% RH are about 4 times that of Form CSIV. The weight gains of Form CSIV from 0 to 60% RH and from 0 to 70% RH are 0.23% and 0.27%, the weight gains of amorphous from 0 to 60% RH and from 0 to 70% RH are 0.94% and 1.18%, respectively.

In one aspect, poor hygroscopicity tends to cause chemical degradation and polymorph transformation, which directly affects the physical and chemical stability of the drug substance. In addition, poor hygroscopicity will reduce the flowability of the drug substance, thereby affecting the processing of the drug substance.

In another aspect, drug substance with poor hygroscopicity requires low humidity environment during production and storage, which puts strict requirements on production and imposes higher costs. More importantly, poor hygroscopicity is likely to cause variation in the content of active pharmaceutical ingredients in the drug product, thus affecting drug product quality.

Form CSIV provided by the present disclosure with better hygroscopicity is not demanding on the production and storage conditions, which reduces the cost of production, storage and quality control, and has strong economic value.

(2) Compared with prior arts, Form CSIV of the present disclosure has no solvent residue. Form CSIV has no solvent residue while prior art amorphous contains 2.70% ethyl acetate, which is far beyond the residual solvent limit specified in the Pharmacopoeia (0.5%). Ethyl acetate has toxic side effects on the central nervous system, and long-term exposure can cause conjunctival irritation and corneal opacity, and even cause liver and kidney congestion. Compared with prior art amorphous, the preparation process of Form CSIV is solvent-free and there is no solvent residue in Form CSIV, which can not only reduce the drug toxicity effect of the raw material drug due to the solvent residue, but also reduce the production cost.

(3) Form CSIV provided by the present disclosure has good appearance. Form CSIV has good powder dispersibility, which is beneficial to transfer and reduce weight loss in industrial production.

(4) From CSIV drug substance of the present disclosure has good stability. Crystalline state of Form CSIV drug substance doesn't change for at least 3 months when stored under the condition of 25° C./60% RH with open and sealed package. The chemical purity remains substantially unchanged during storage. The results show that From CSIV drug substance has good stability under long term condition, which is beneficial to the drug storage.

Meanwhile, crystalline state of Form CSIV drug substance doesn't change for at least 3 months when stored under the condition of 40° C./75% RH with open and sealed package, and the chemical purity remains substantially unchanged during storage. The crystalline form of Form CSIV drug substance doesn't change for at least one month when stored under the condition of 60° C./75% RH with open and sealed package, and the chemical purity remains substantially unchanged during storage. These results show that Form CSIV drug substance has good stability under accelerated and stress conditions. Drug substance will go through high temperature and high humidity conditions caused by different season, regional climate and environment during storage, transportation, and manufacturing processes. Therefore, good stability under accelerated and stress conditions is of great importance to the drug development. Form CSIV drug substance has good stability under stress condition, which is beneficial to avoid the impact on drug quality due to crystal transformation or decrease in purity during drug storage.

Meanwhile, Form CSIV has good physical stability under mechanical force. Form CSIV drug substance has good physical stability after tableting and grinding. Grinding and pulverization are often required in the drug manufacturing process. Good physical stability of the drug substance can reduce the risk of crystallinity decrease and crystal transformation during the drug production process. Form CSIV has good physical stability under different pressures, which is beneficial to keep crystalline form unchanged during tableting process.

(5) Form CSIV of the present disclosure shows low adhesiveness. Low adhesiveness can reduce the agglomeration of drug substance and effectively improve the adhesion to roller and tooling during dry-granulation and compression process. It is conducive to the dispersion of drug substance with excipients and improve the blend uniformity of the mixing of materials, which ultimately improves product quality.

DETAILED DESCRIPTION OF PREFERRED EMBODIMENTS

Figure 1:
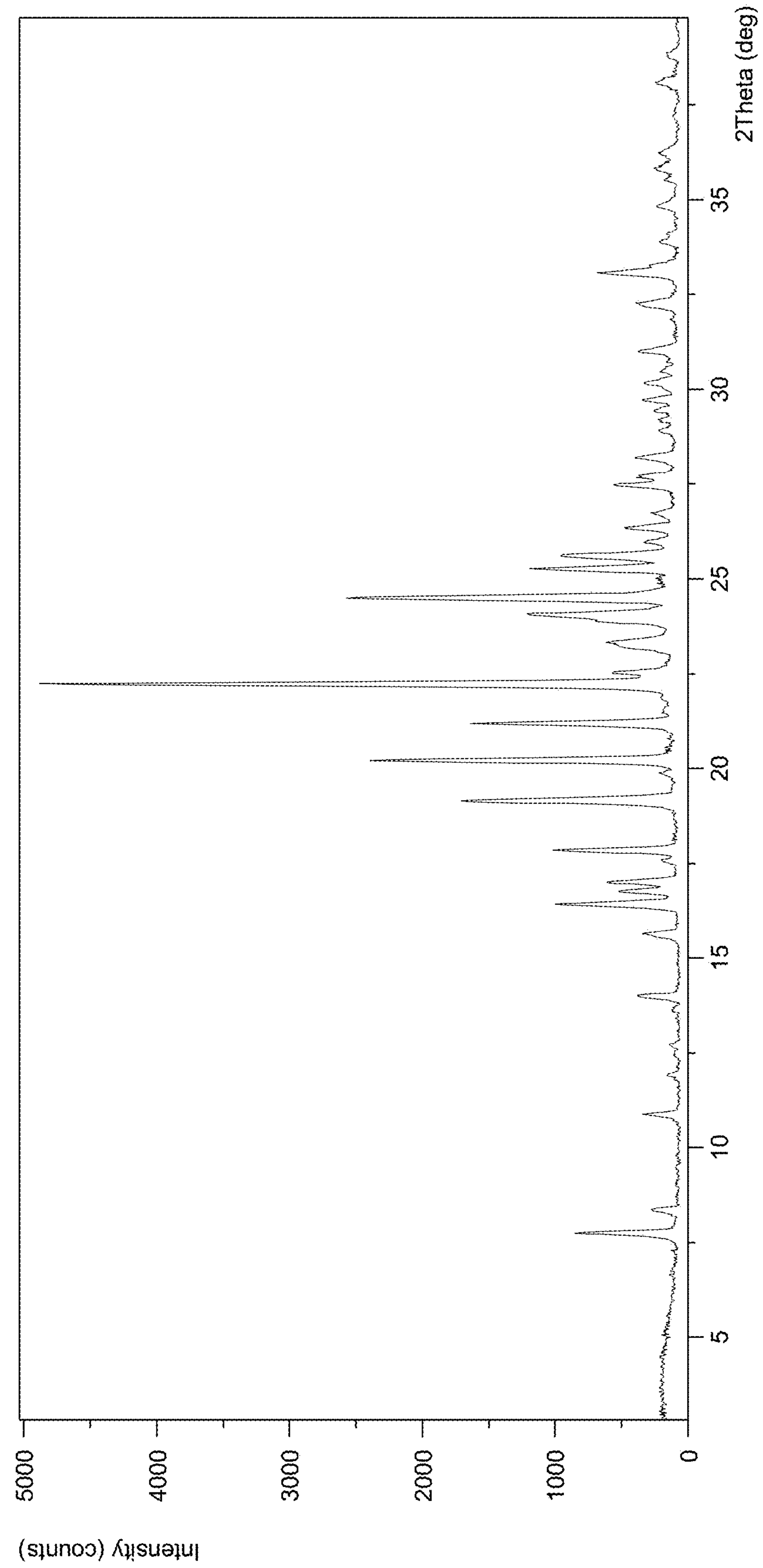
FIG. 1 shows an XRPD pattern of Form CSI according to example 2.

The present disclosure is further illustrated by the following examples which describe the preparation and use of the crystalline forms of the present disclosure in detail. It is obvious to those skilled in the art that changes in the materials and methods can be accomplished without departing from the scope of the present disclosure.

The abbreviations used in the present disclosure are explained as follows:

XRPD : X-ray Powder Diffraction

TGA: Thermo Gravimetric Analysis

DSC: Differential Scanning calorimetry $^1$H NMR: Proton Nuclear Magnetic Resonance DVS: Dynamic Vapor Sorption PSD: Particle Size Distribution HPLC: High Performance Liquid Chromatography RH: Relative humidity Instruments and methods used for data collection:

X-ray powder diffraction patterns in the present disclosure were acquired by a Bruker X-ray powder diffractometer. The parameters of the X-ray powder diffraction method of the present disclosure are as follows:

X-Ray source: Cu, Kα

Kα1 (Å): 1.54060; Kα2 (Å): 1.54439

Kα2/Kα1 intensity ratio: 0.50

Thermo gravimetric analysis (TGA) data in the present disclosure were acquired by a TA Q500. The parameters of the TGA method of the present disclosure are as follows:

Heating rate: 10° C./min

Purge gas: $N_2$

Differential scanning calorimetry (DSC) data in the present disclosure were acquired by a TA Q2000. The parameters of the DSC method of the present disclosure are as follows:

Heating rate: 10° C./min

Purge gas: $N_2$

Proton nuclear magnetic resonance spectrum data ($^1$H NMR) were collected from a Bruker Avance II DMX 400M Hz NMR spectrometer. 1-5 mg of sample was weighed and dissolved with 0.5 mL of deuterated dimethyl sulfoxide to obtain a solution with a concentration of 2-10 mg/mL.

Dynamic Vapor Sorption (DVS) was measured via an SMS (Surface Measurement Systems Ltd.) intrinsic DVS instrument. The instrument control software is DVS-Intrinsic control software. Typical Parameters for DVS test are as follows:

Temperature: 25° C.

Gas and flow rate: $N_2$, 200 mL/min

RH range: 0% RH to 95% RH

Single crystal X-ray diffraction (SC-XRD) in the present disclosure was acquired by an Agilent Gemini A diffractometer equipped with a CMOS detector and microfocal enclosed X-ray generator (Cu/Kα λ=1.54184 Å). The single crystal was kept at 293(2) K during data collection.

The parameters of related substance detection in the present disclosure is shown in Table 2.

TABLE 2

| | | |
|---|---|---|
| Instrument | Waters ACQUITY H-Class with PDA detector | |
| Column | ACE Excel 3 C18, 4.6 * 100 mm, 3.0 μm | |
| Mobile phase | A: Acetonitrile: Water (pH 3.0, phosphoric acid) = 50:950 (v/v)<br>B: Acetonitrile | |
| | Time (min) | % A |
| Gradient | 0.0 | 60 |
| | 0.5 | 60 |
| | 5.0 | 20 |
| | 7.0 | 10 |
| | 12.0 | 10 |
| | 12.1 | 60 |
| | 18.0 | 60 |
| Run time | 18.0 min | |
| Post time | 0 min | |
| Flow rate | 1.0 mL/min | |
| Injection volume | 1 μL | |
| Detector wavelength | 220 nm | |
| Column temperature | 40° C. | |
| Sample temperature | Room Temperature | |
| Diluent | Acetonitrile | |

The particle size distribution data in the present disclosure were acquired by an Mastersizer 3000 laser particle size analyzer of Malvern. The test was carried out in wet mode, using a Hydro MV dispersion device, and the dispersant was Isopar G. The parameters are shown in Table 3.

TABLE 3

| | |
|---|---|
| Size distribution: Volume | Measurement duration: 10 s |
| Dispersant name: Isopar G | Particle type: Non-spherical |
| Number of measurements: 3 | Fluid refractive index: 1.42 |
| Absorption index: 0.1 | Ultrasonication power/time: 30 W/30 s |
| Particle refractive index: 1.52 | Stirrer speed: 2000 rpm |

In the present disclosure, said "stirring" is accomplished by using a conventional method in the field such as magnetic stirring or mechanical stirring and the stirring speed is 50 to 1800 r/min. Preferably the magnetic stirring speed is 300 to 900 r/min and mechanical stirring speed is 100 to 300 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "evaporating" is accomplished by using a conventional method in the field such as slow evaporation or rapid evaporation. Slow evaporation is accomplished in a container covered by a sealing film with pinholes. Rapid evaporation is accomplished in an open container.

The "concentrated under reduced pressure" accomplished by using a conventional method in the field. For example, the operation of concentrated under reduced pressure is to rotate the flask containing solution at a constant speed at a certain temperature and a certain reduced pressure to evaporate the solvent.

Said "room temperature" is not a specific temperature, but a temperature range of 10-30° C.

Said "characteristic peak" refers to a representative diffraction peak used to distinguish crystals, which usually can have a deviation of ±0.2° using CuKα radiation.

In the present disclosure, "crystal" or "crystalline form" refers to the crystal or the crystalline form being identified by the X-ray diffraction pattern shown herein. Those skilled in the art are able to understand that the X-ray powder diffraction pattern depend on the instrument conditions, the sample preparation and the purity of samples. The relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. Thus, it will be understood by those skilled in the art that a crystalline form of the present disclosure is not necessarily to have exactly the same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CSI, Form CSII or Form CSIV of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and furthermore specifically less than 1% (w/w).

In the present disclosure, the term "about" when referring to a measurable value such as weight, time, temperature, and the like, is meant to encompass variations of ±10%, ±5%, ±1%, ±0.5%, or even ±0.1% of the specified amount.

Unless otherwise specified, the following examples were conducted at room temperature.

According to the present disclosure, Compound I used as raw materials include, but are not limited to solid (crystalline and amorphous), semisolid, wax, oil, liquid form or solution. Preferably, Compound I used as the raw material is a solid.

Raw materials of Compound I used in the following examples were prepared by prior arts, for example, the method disclosed in WO2007026097A1.

Example 1 Characterization of Compound I Solvates 1,4-dioxane solvate, chloroform solvate and tetrahydrofuran solvate of Compound I were characterized by TGA, DSC, and $^1$H NMR. The results are listed in Table 4.

TABLE 4

| Form | Preparation method | TGA | DSC | $^1$H NMR |
|---|---|---|---|---|
| 1,4-dioxane solvate | 23.8 mg of Compound I was weighed into a glass vial followed by adding 1 mL of 1,4-dioxane to dissolve the solid. The solution was filtered. The filtrate was divided into two parts, and one of the filtrate was put at 50° C. for rapid evaporation. | About 10.1% weight loss when heated to 200° C. | Two endothermic peaks at around 130.1° C. and 178.2° C., and an exothermic peak at around 135.8° C. | 0.56 molar equivalents of 1,4-dioxane per mole of 1,4-dioxane solvate. |
| chloroform solvate | 10.8 mg of 1,4-dioxane solvate was weighed into a glass vial followed by adding 0.3 mL of chloroform, and the system was stirred at −20° C. for one day. A solid was isolated and dried under vacuum at room temperature for 2 hours. | About 3.3% weight loss when heated to 230° C. | Two endothermic peaks at around 96.8° C. and 179.2° C., and an exothermic peak at around 122.8° C. | 0.14 molar equivalents of chloroform per mole of chloroform solvate. |

TABLE 4-continued

| Form | Preparation method | TGA | DSC | $^1$H NMR |
|---|---|---|---|---|
| tetrahydrofuran solvate | 9.5 mg of Compound I was weighed into a glass vial followed by adding 1 mL of tetrahydrofuran/chloroform (1:1, v/v) to dissolve the solid. The solution was filtered. The filtrate was put at 50° C. for slow evaporation. | About 6.0% weight loss when heated to 120° C. | Three endothermic peaks around 103.7° C., 168.4° C. and 179.2° C., and two exothermic peaks at around 109.7° C. and 156.2° C. | 0.37 molar equivalents of tetrahydrofuran and 0.05 molar equivalents of chloroform per mole of tetrahydrofuran solvate. |

Rapid evaporation: evaporate with open lid.

Slow evaporation: seal the container with aluminum foil, poke holes, and stand to evaporate.

Example 2 Preparation of Form CSI

According to Table 5, a certain amount of Compound I was weighed into a glass vial, followed by adding 0.3 mL of corresponding solvent, and then stirred at room temperature. The obtained solid was separated and labeled as Samples 1-2. Samples 1-2 were confirmed to be Form CSI of the present disclosure.

The XRPD pattern of Sample 1 is substantially as depicted in FIG. 1 and the XRPD data are listed in Table 6.

Figure 2:
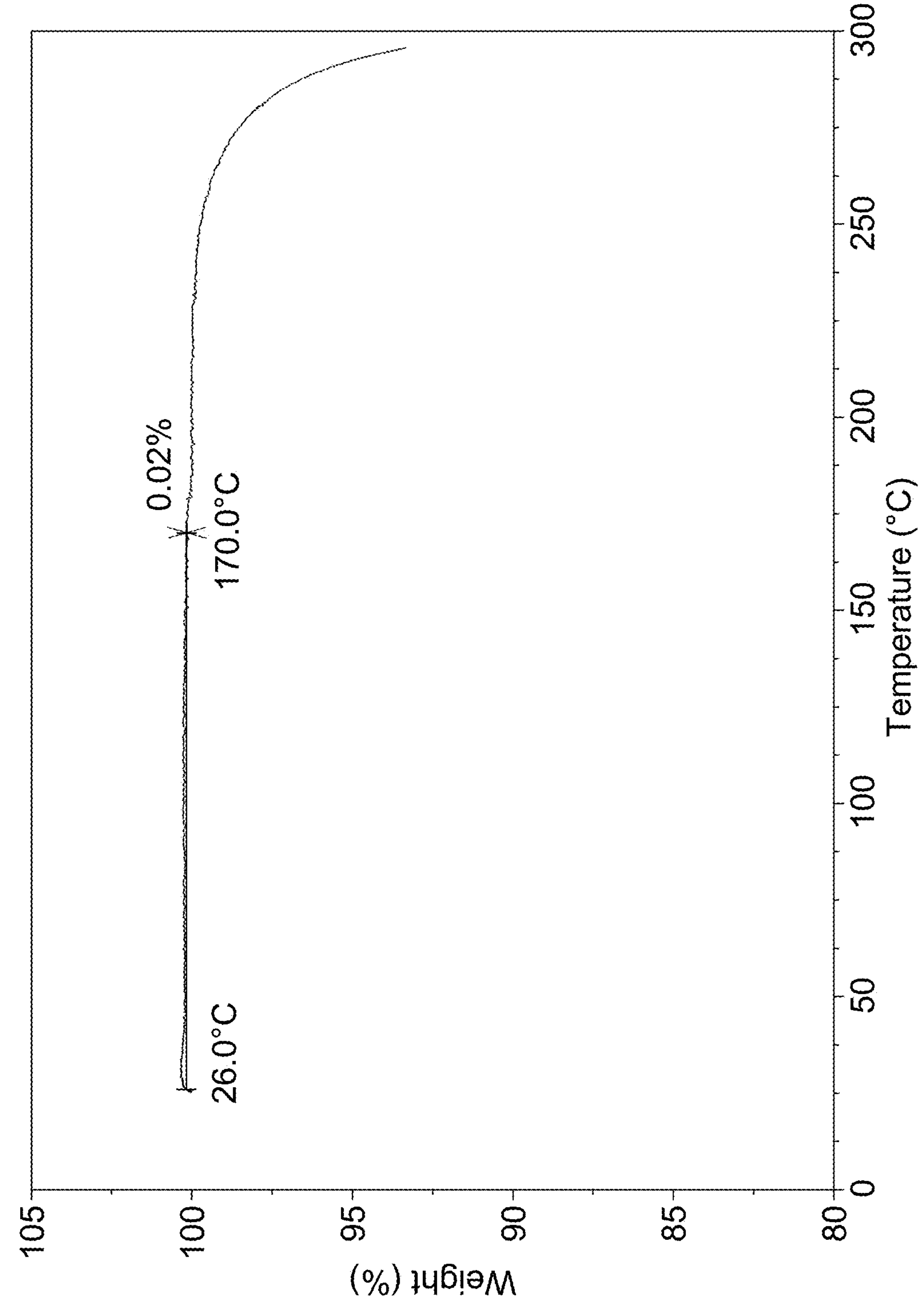
FIG. 2 shows a TGA curve of Form CSI according to example 2.

The TGA curve of Sample 1 is substantially as depicted in FIG. 2, which shows about 0.02% weight loss when heated to 170° C.

The $^1$N NMR data of Sample 1 are: $^1$H NMR (400 MHz, DMSO) δ 12.13 (s, 1H), 9.66 (s, 1H), 8.97 (d, J=1.8 Hz, 1H), 8.20 (d, J=8.7 Hz, 1H), 8.09 (d, J=8.9 Hz, 1H), 7.85 (dd, J=8.7, 1.9 Hz, 1H), 7.58 (d, J=2.0 Hz, 1H), 7.32 (dd, J=8.9, 2.1 Hz, 1H), 6.62 (s, 1H), 3.09 (t, J=7.4 Hz, 2H), 2.36 (t, J=7.3 Hz, 2H), 1.99-1.90 (m, 2H).

TABLE 5

| Sample | Weight of Compound I (mg) | Solvent | Stirring time | Solid form |
|---|---|---|---|---|
| 1 | 11.4 | ethanol | 24 hours | Form CSI |
| 2 | 10.1 | methyl tert-butyl ether | 2 hours | Form CSI |

TABLE 6

| Diffraction angle 2θ (°) | d spacing (Å) | Relative Intensity (%) |
|---|---|---|
| 7.74 | 11.42 | 15.72 |
| 8.35 | 10.59 | 3.94 |
| 10.87 | 8.14 | 5.73 |
| 11.91 | 7.43 | 1.87 |

TABLE 6-continued

| Diffraction angle 2θ (°) | d spacing (Å) | Relative Intensity (%) |
|---|---|---|
| 13.98 | 6.33 | 6.50 |
| 15.63 | 5.67 | 5.67 |
| 16.41 | 5.40 | 19.10 |
| 16.75 | 5.29 | 9.51 |
| 16.99 | 5.22 | 11.38 |
| 17.83 | 4.97 | 19.60 |
| 19.13 | 4.64 | 33.98 |
| 20.20 | 4.40 | 48.57 |
| 21.18 | 4.20 | 32.67 |
| 22.22 | 4.00 | 100.00 |
| 22.52 | 3.95 | 10.41 |
| 23.29 | 3.82 | 10.56 |
| 24.05 | 3.70 | 23.80 |
| 24.49 | 3.64 | 52.12 |
| 25.25 | 3.53 | 23.23 |
| 25.60 | 3.48 | 18.41 |
| 25.97 | 3.43 | 5.40 |
| 26.33 | 3.39 | 8.44 |
| 27.47 | 3.25 | 10.09 |
| 27.69 | 3.22 | 6.09 |
| 28.19 | 3.17 | 6.87 |
| 29.71 | 3.01 | 5.78 |
| 30.16 | 2.96 | 5.47 |
| 30.99 | 2.89 | 6.30 |
| 32.24 | 2.78 | 6.37 |
| 33.06 | 2.71 | 12.74 |
| 33.93 | 2.64 | 2.37 |
| 34.82 | 2.58 | 3.40 |
| 35.81 | 2.51 | 3.53 |
| 36.22 | 2.48 | 3.00 |
| 38.09 | 2.36 | 3.45 |
| 38.80 | 2.32 | 1.81 |

Example 3 Preparation of Form CSI

According to Table 7, a certain amount of Compound I was weighed into a glass vial, followed by adding a certain volume of corresponding solvent to dissolve the solid. The solution was left for evaporation. The obtained solid was labeled as Samples 1-2. Samples 1-2 were confirmed to be Form CSI of the present disclosure.

Figure 3:
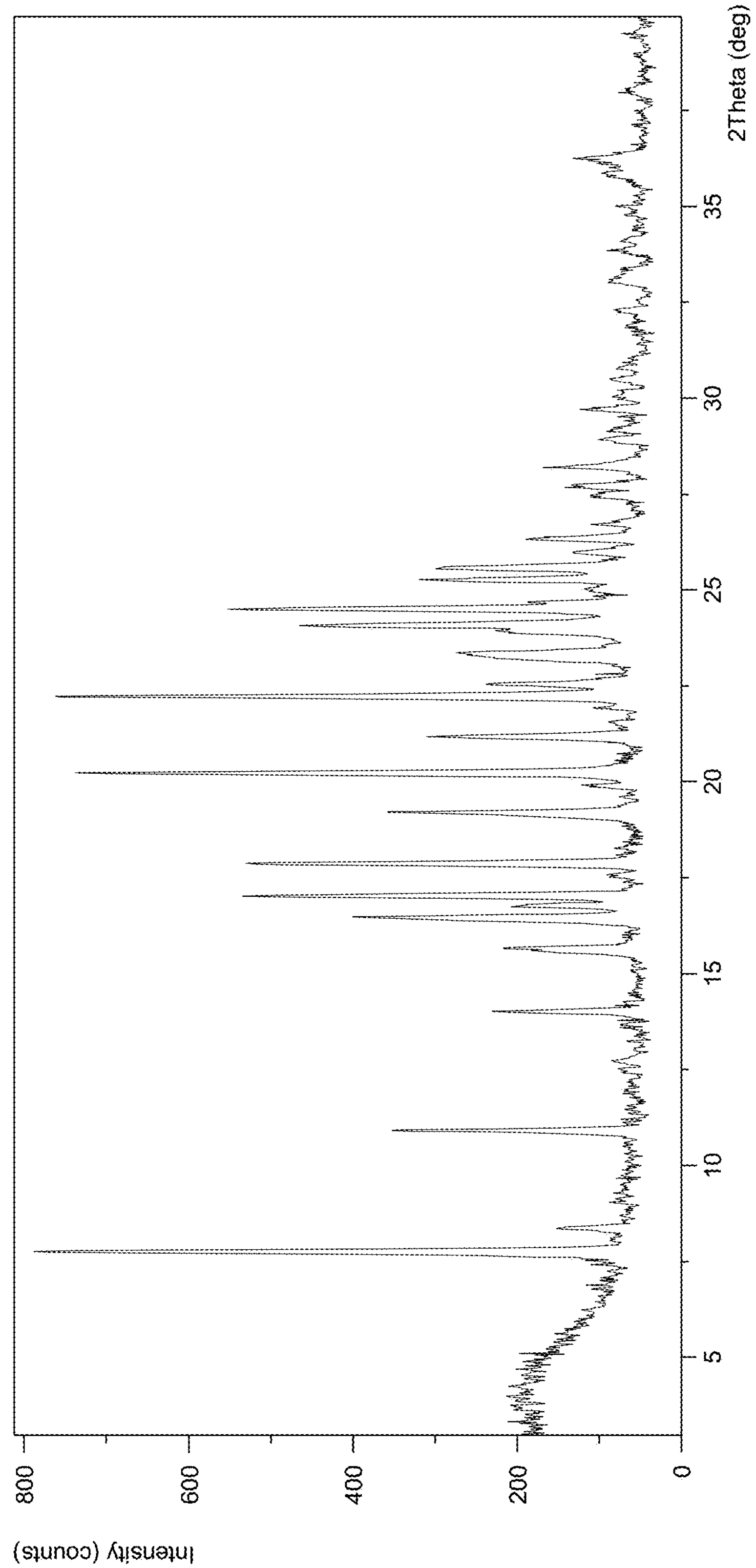
FIG. 3 shows an XRPD pattern of Form CSI according to example 3.

The XRPD pattern of Sample 1 is substantially as depicted in FIG. 3 and the XRPD data are listed in Table 8.

TABLE 7

| Sample | Weight of Compound I (mg) | Solvent | volume (mL) | Clear solution volume (mL) | Evaporation temperature | Solid form |
|---|---|---|---|---|---|---|
| 1 | 4.3 | 2-Methyltetrahydrofuran | 0.2 | 0.2 | 50° C. | Form CSI |
| 2 | 4.4 | Toluene | 3.5 | 3.5 | 50° C. | Form CSI |

TABLE 8

| Diffraction angle 2θ (°) | d spacing (Å) | Relative intensity (%) |
|---|---|---|
| 7.74 | 11.42 | 98.97 |
| 8.36 | 10.58 | 10.65 |
| 10.90 | 8.12 | 40.91 |
| 12.71 | 6.97 | 3.82 |
| 14.00 | 6.33 | 23.50 |
| 15.66 | 5.66 | 23.11 |
| 16.45 | 5.39 | 46.69 |
| 16.75 | 5.29 | 20.55 |
| 17.01 | 5.21 | 67.29 |
| 17.86 | 4.97 | 67.05 |
| 19.19 | 4.62 | 43.51 |
| 20.22 | 4.39 | 96.43 |
| 21.17 | 4.20 | 36.31 |
| 22.22 | 4.00 | 100.00 |
| 22.54 | 3.94 | 26.39 |
| 23.33 | 3.81 | 30.56 |
| 24.07 | 3.70 | 58.17 |
| 24.49 | 3.63 | 69.35 |
| 25.25 | 3.53 | 36.00 |
| 25.57 | 3.48 | 34.05 |
| 25.96 | 3.43 | 11.77 |
| 26.31 | 3.39 | 19.66 |
| 26.72 | 3.34 | 7.02 |
| 27.45 | 3.25 | 8.51 |
| 27.70 | 3.22 | 11.52 |
| 28.19 | 3.17 | 16.81 |
| 28.90 | 3.09 | 6.49 |
| 29.18 | 3.06 | 5.22 |
| 29.70 | 3.01 | 10.87 |
| 30.48 | 2.93 | 5.37 |
| 32.27 | 2.77 | 4.88 |
| 33.06 | 2.71 | 5.77 |
| 33.84 | 2.65 | 5.02 |
| 36.22 | 2.48 | 10.16 |
| 38.00 | 2.37 | 2.66 |

Example 4 Single Crystal Growth of Form CSI 375.9 mg of Compound I solid was dissolved into 22 mL of acetone. The solution was filtered. 10 mL of acetonitrile was added into 10 mL of the filtrate. The solution was filtered again. 3.2 mL of the filtrate was evaporated at room temperature for 9 days to obtain single crystals of Form CSI.

Figure 4:
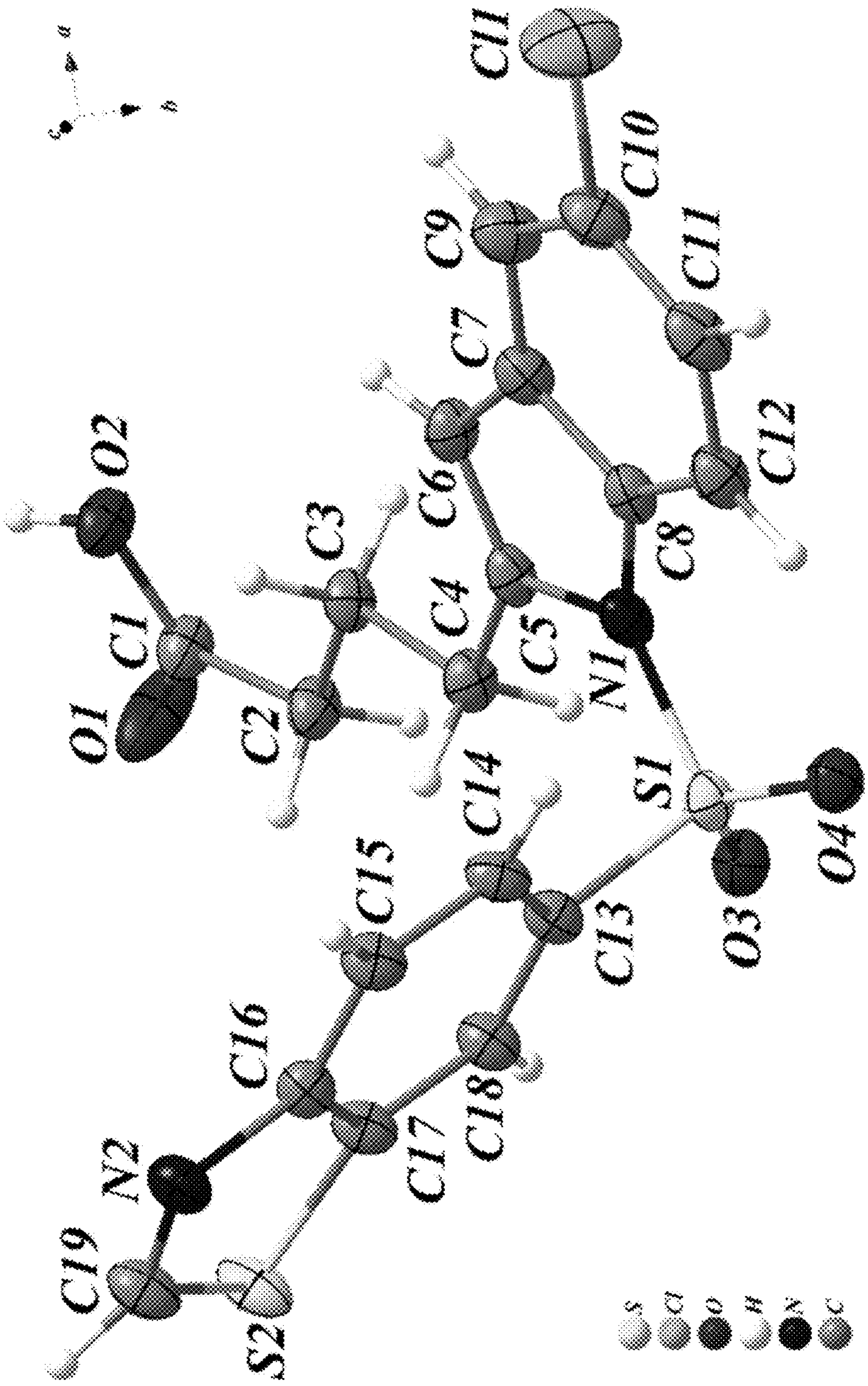
FIG. 4 shows an asymmetric unit of Form CSI single crystal structure according to example 4.

The unit cell parameters of Form CSI were obtained by X-ray single crystal diffraction and analysis, as shown in Table 9. The asymmetric unit of Form CSI is shown in FIG. 4. The results show that the asymmetric unit of Form CSI is composed of one Compound I molecule. Form CSI is an anhydrate.

TABLE 9

| | |
|---|---|
| Empirical formula | $C_{19}H_{15}ClN_2O_4S_2$ |
| Formula weight | 434.90 |
| Temperature | 293(2) K |
| X-Ray | Cu/Kα (λ = 1.54184 Å) |
| Crystal system | monoclinic |
| Space group | $P2_1/n$ |
| Unit cell dimensions | a = 14.8715(9) Å<br>b = 7.8511(6) Å<br>c = 16.2886(8) Å<br>α = 90°<br>β = 94.332(5)°<br>γ = 90° |
| Volume | 1896.4(2) $Å^3$ |
| Number of molecules per unit cell (Z) | 4 |
| Calculated density | 1.523 g/$cm^3$ |

Example 5 Preparation of Form CSII

According to Table 10, a certain amount of Compound I was weighed into a glass vial, followed by adding a certain volume of solvent to form a clear solution. A certain volume of the clear solution was evaporated at 50° C. to obtain a solid. The obtained solid was labeled as Samples 1-4. Samples 1-4 were confirmed to be Form CSII of the present disclosure.

Figure 5:
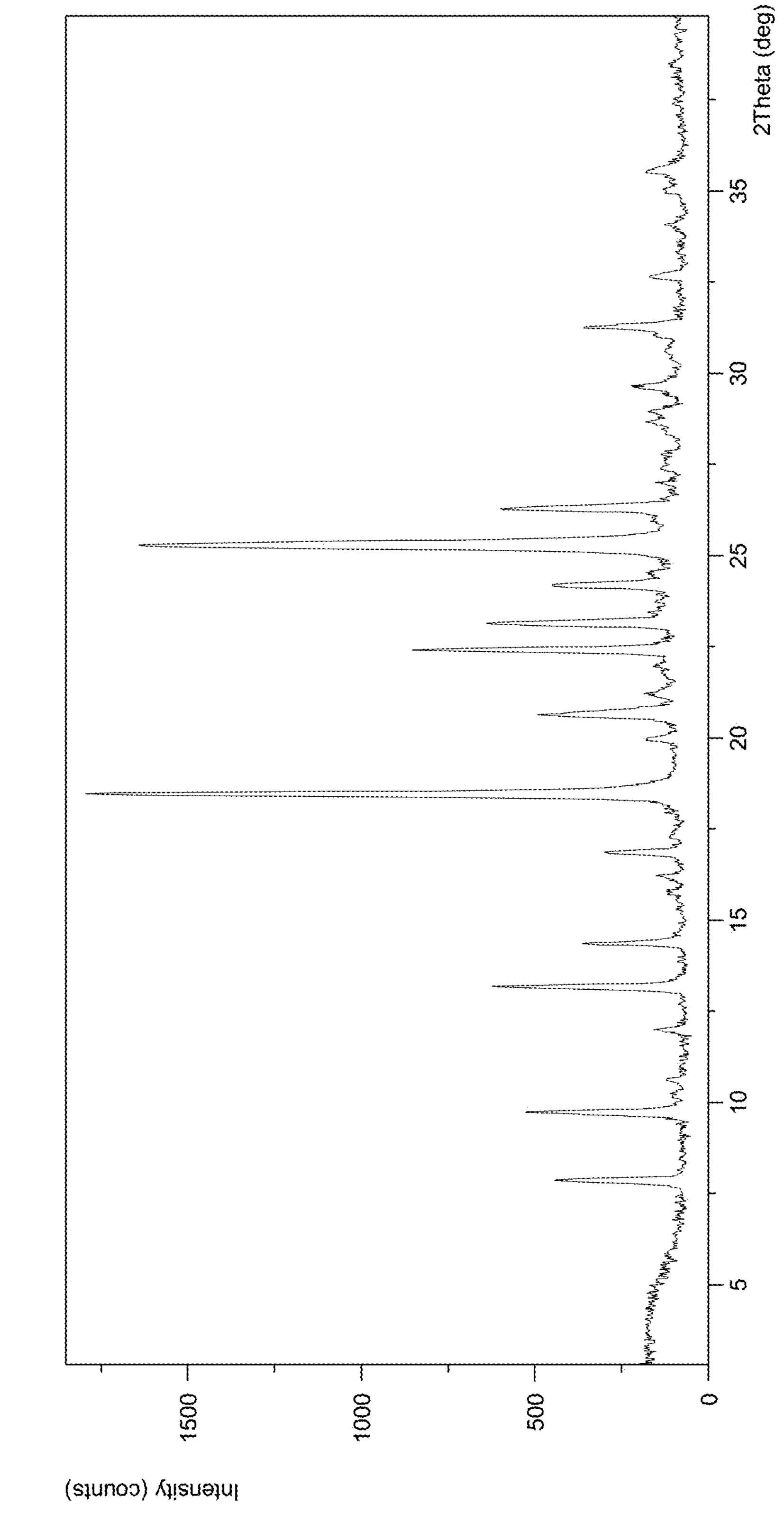
FIG. 5 shows an XRPD pattern of Form CSII according to example 5.

The XRPD pattern of Sample 4 is substantially as depicted in FIG. 5 and the XRPD data are listed in Table 11.

Figure 6:
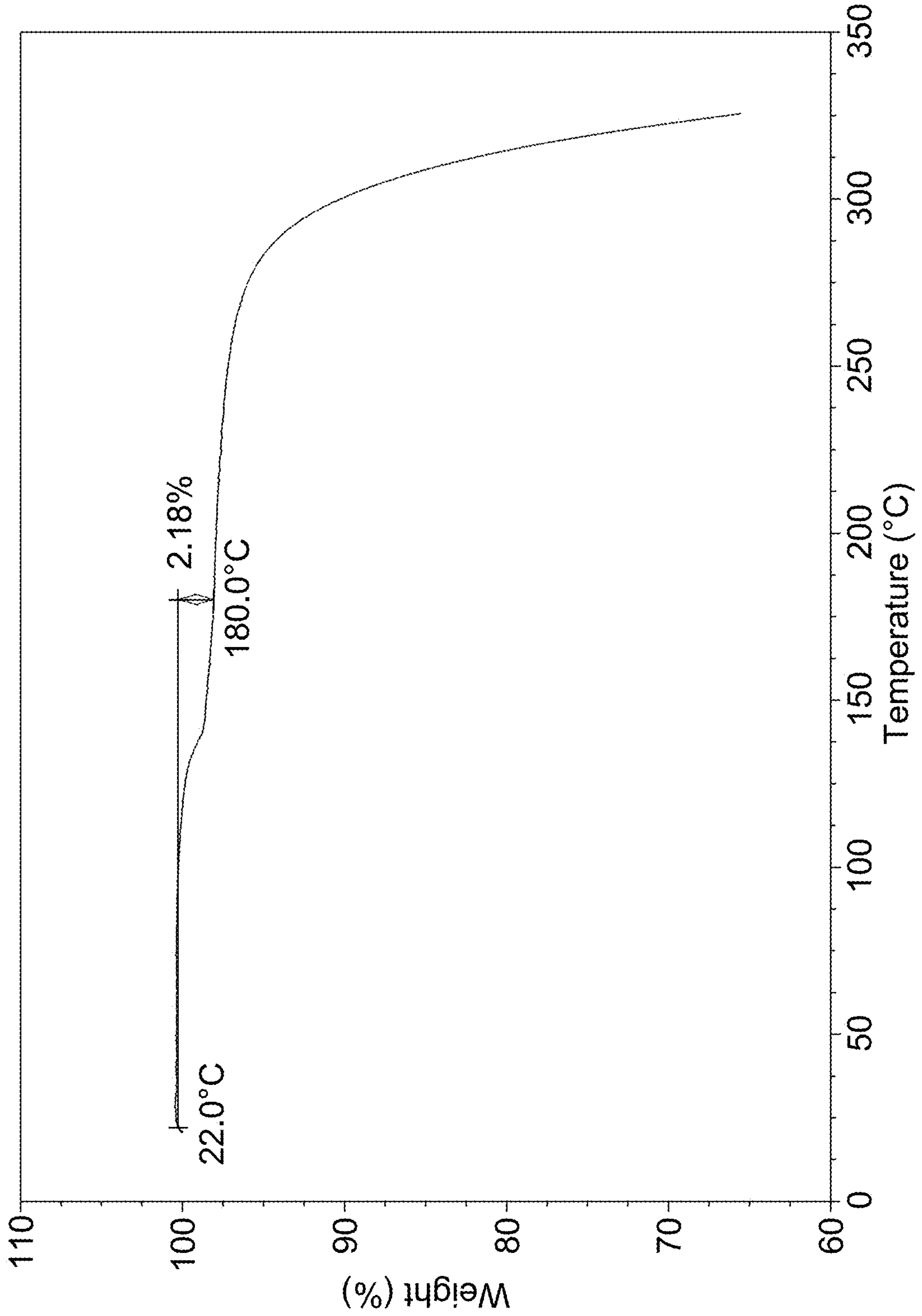
FIG. 6 shows a TGA curve of Form CSII according to example 5.

The TGA curve of Sample 4 is substantially as depicted in FIG. 6, which shows about 2.2% weight loss when heated to 180° C.

Figure 7:
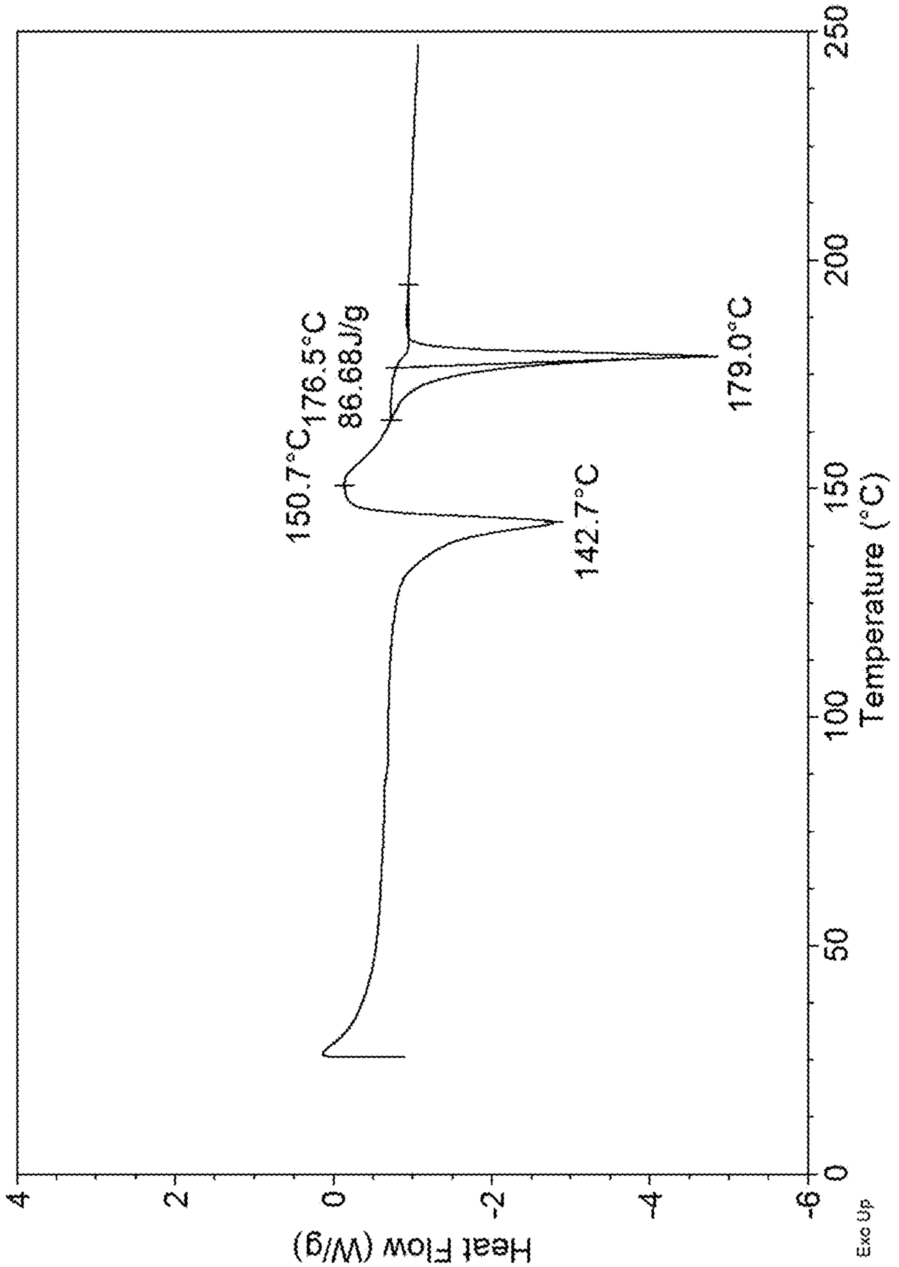
FIG. 7 shows a DSC curve of Form CSII according to example 5.

The DSC curve of Sample 4 is substantially as depicted in FIG. 7, which shows an endothermic peak at around 143° C., an exothermic peak at around 151° C., and an endothermic peak at around 177° C. (onset temperature).

TABLE 10

| Sample | Weight of Compound I (mg) | Solvent | Solvent volume (mL) | Filtrate volume (mL) | Solid form |
|---|---|---|---|---|---|
| 1 | 5.0 | methanol | 3.6 | 3.6 | Form CSII |
| 2 | 4.6 | n-Propanol | 3.6 | 3.6 | Form CSII |
| 3 | 24.6 | 2-Butanone | 2 | 1.0 | Form CSII |
| 4 | 28.7 | methanol | 21 | 3.5 | Form CSII |

TABLE 11

| Diffraction angle 2θ (°) | d spacing (Å) | Relative intensity (%) |
|---|---|---|
| 7.86 | 11.25 | 21.58 |
| 9.73 | 9.09 | 26.96 |
| 10.61 | 8.34 | 3.01 |
| 11.99 | 7.38 | 4.89 |
| 13.16 | 6.73 | 31.90 |
| 14.35 | 6.17 | 16.79 |
| 15.76 | 5.62 | 2.79 |
| 16.18 | 5.48 | 3.60 |
| 16.84 | 5.26 | 13.20 |
| 18.45 | 4.81 | 100.00 |
| 19.96 | 4.45 | 6.09 |
| 20.61 | 4.31 | 24.56 |
| 21.19 | 4.19 | 5.54 |
| 22.40 | 3.97 | 45.46 |
| 23.13 | 3.85 | 33.11 |
| 24.16 | 3.68 | 22.28 |
| 25.27 | 3.53 | 91.43 |
| 26.28 | 3.39 | 30.70 |
| 26.98 | 3.31 | 4.28 |
| 27.39 | 3.26 | 3.78 |
| 27.68 | 3.22 | 2.79 |
| 28.65 | 3.12 | 5.87 |
| 28.92 | 3.09 | 5.64 |
| 29.62 | 3.02 | 8.04 |
| 31.25 | 2.86 | 16.72 |
| 32.63 | 2.74 | 5.66 |
| 34.04 | 2.63 | 2.01 |
| 35.00 | 2.56 | 3.07 |
| 35.54 | 2.53 | 5.98 |
| 38.46 | 2.34 | 1.44 |

Example 6 Preparation of Form CSII 112.4 mg of Compound I was weighed into a glass vial, followed by adding 5 mL of tetrahydrofuran and 5 mL of acetonitrile. The system was filtered. 1.5 mL of the filtrate was evaporated at room temperature for 2 days to obtain a solid. The obtained solid was dried under vacuum at 50° C. for 2 weeks to obtain a crystalline solid.

Figure 8:
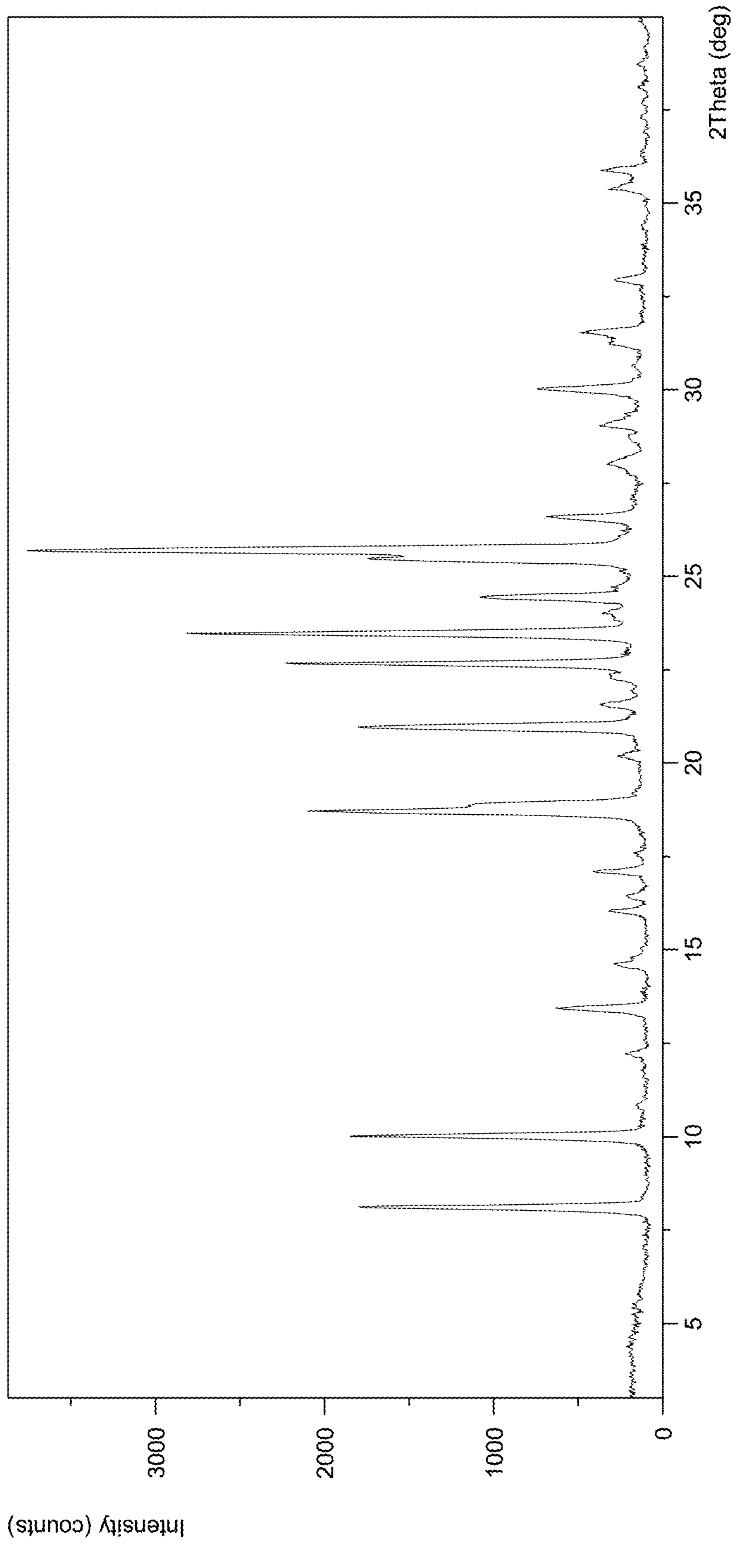
FIG. 8 shows an XRPD pattern of Form CSII according to example 6.

The crystalline solid was confirmed to be Form CSII. The XRPD pattern is substantially as depicted in FIG. 8 and the XRPD data are listed in Table 12.

TABLE 12

| Diffraction angle 2θ (°) | d spacing (Å) | Relative intensity (%) |
|---|---|---|
| 7.88 | 11.22 | 46.72 |
| 9.79 | 9.04 | 48.00 |
| 12.00 | 7.38 | 3.32 |
| 13.21 | 6.70 | 14.76 |
| 14.39 | 6.16 | 5.21 |
| 15.82 | 5.60 | 6.04 |
| 16.22 | 5.46 | 3.24 |
| 16.87 | 5.26 | 8.70 |
| 18.49 | 4.80 | 55.22 |
| 18.69 | 4.75 | 26.90 |
| 19.97 | 4.45 | 4.37 |
| 20.74 | 4.28 | 46.84 |
| 21.34 | 4.16 | 7.71 |
| 22.09 | 4.02 | 6.07 |
| 22.44 | 3.96 | 58.72 |
| 23.24 | 3.83 | 74.24 |
| 23.81 | 3.74 | 6.90 |
| 24.21 | 3.68 | 26.96 |
| 25.25 | 3.53 | 45.31 |
| 25.47 | 3.50 | 100.00 |
| 26.36 | 3.38 | 16.21 |
| 27.80 | 3.21 | 6.31 |
| 28.81 | 3.10 | 7.65 |
| 29.79 | 3.00 | 17.84 |
| 31.01 | 2.88 | 5.90 |
| 31.32 | 2.86 | 9.87 |
| 32.71 | 2.74 | 5.30 |
| 34.15 | 2.63 | 0.93 |
| 35.16 | 2.55 | 5.82 |
| 35.64 | 2.52 | 7.56 |
| 38.48 | 2.34 | 1.22 |

Example 7 Preparation of Form CSIV 609.9 mg of Compound I solid was weighed, placed in a vacuum oven, heated to 185° C., and cooled to room temperature to obtain a solid. 19.58 mg of the obtained solid was weighed and placed in a crucible, heated to 140° C., and then cooled to room temperature to obtain a crystalline solid.

Figure 9:
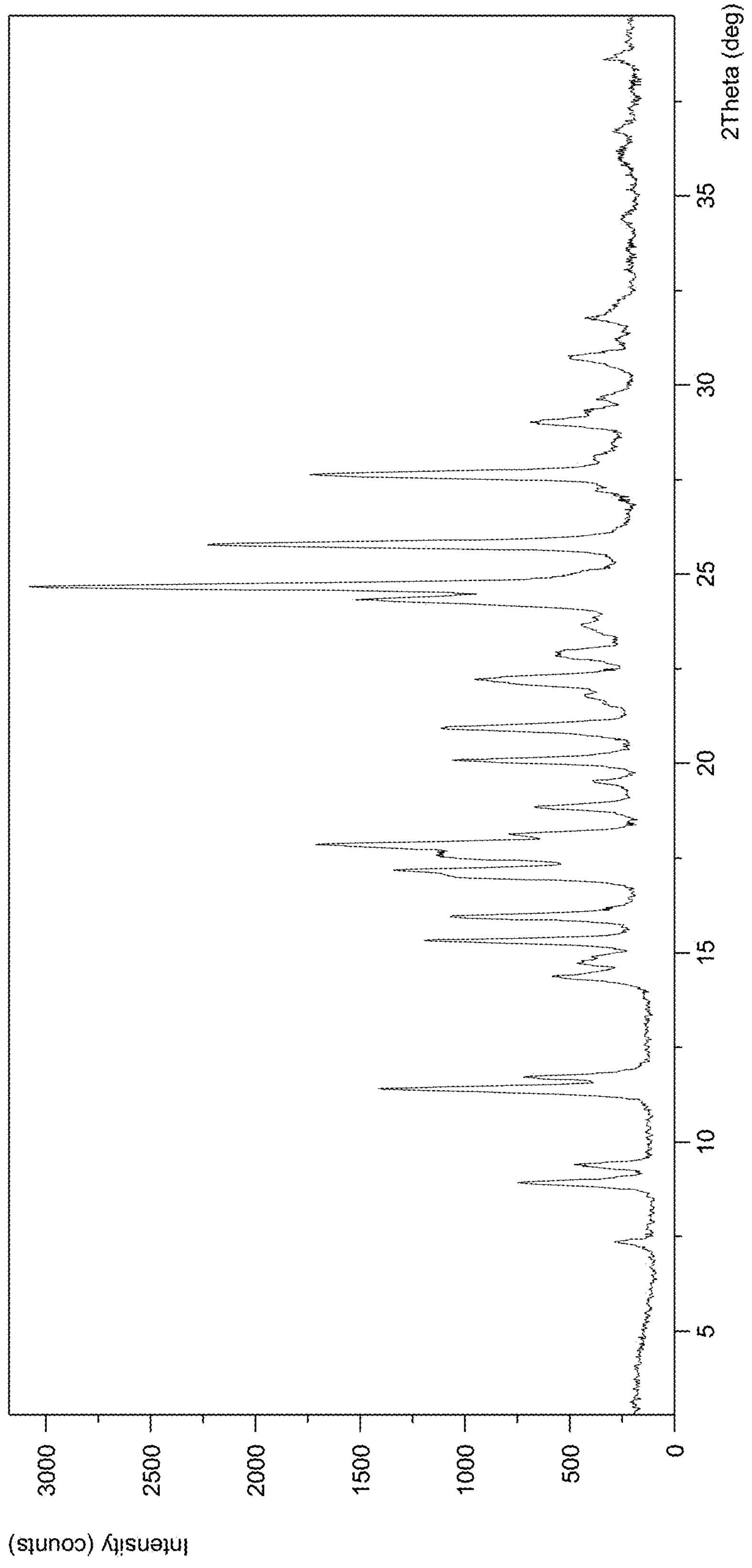
FIG. 9 shows an XRPD pattern of Form CSIV according to example 7.

The crystalline solid was confirmed to be Form CSIV of present disclosure. The XRPD pattern of Form CSIV is substantially as depicted in FIG. 9 and the XRPD data are listed in Table 13.

Figure 10:
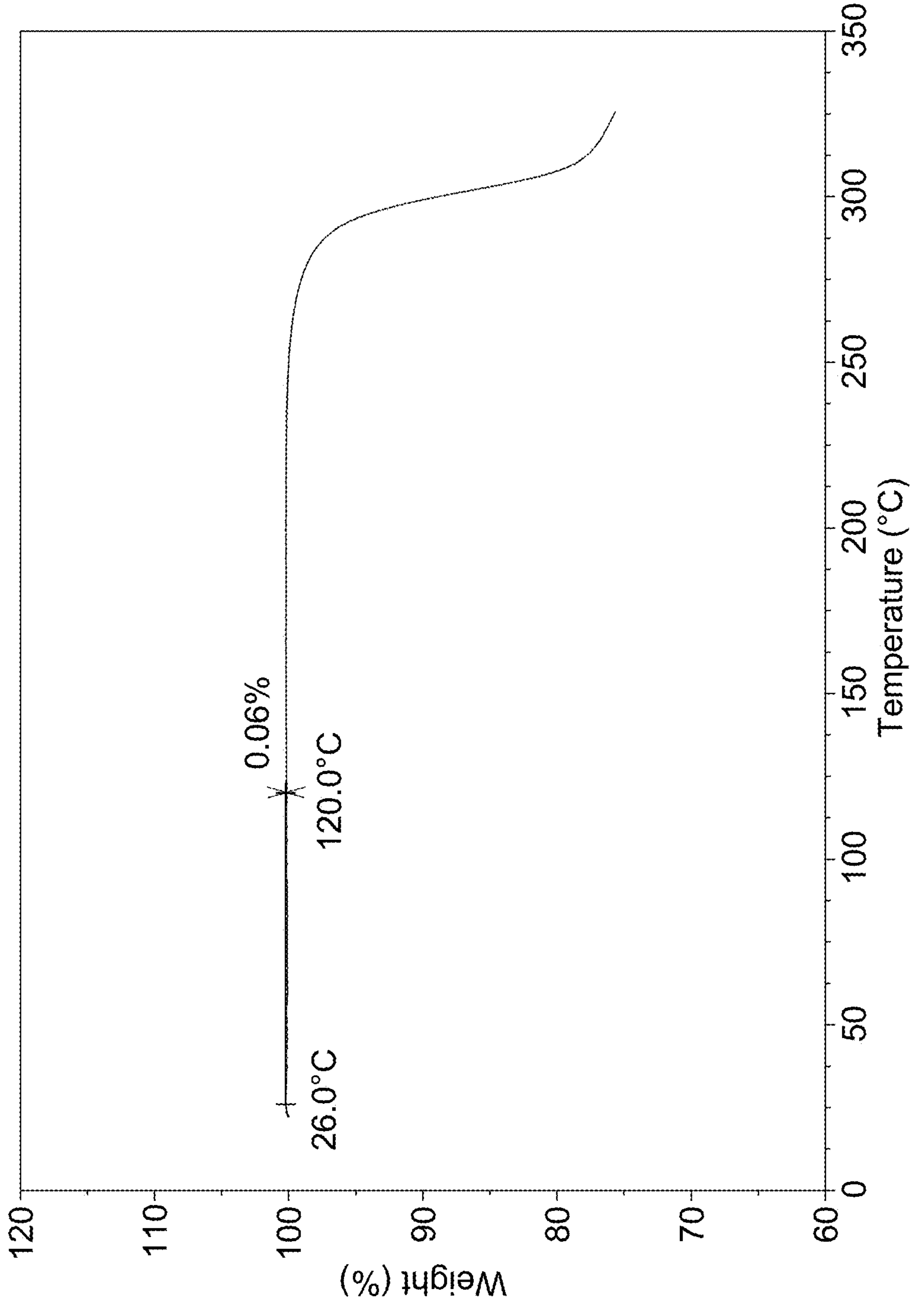
FIG. 10 shows a TGA curve of Form CSIV according to example 7.

The TGA curve of Form CSIV is substantially as depicted in FIG. 10, which shows about 0.06% weight loss when heated to 120° C.

The $^1$H NMR data of Form CSIV are: $^1$H NMR (400 MHz, DMSO-d$^6$) δ 12.12 (s, 1H), 9.65 (s, 1H), 8.97 (d, J=1.9 Hz, 1H), 8.20 (d, J=8.7 Hz, 1H), 8.09 (d, J=8.9 Hz, 1H), 7.84 (dd, J=8.7, 2.1 Hz, 1H), 7.57 (d, J=2.1 Hz, 1H), 7.31 (dd, J=8.9, 2.2 Hz, 1H), 6.62 (s, 1H), 3.08 (t, J=7.4 Hz, 2H), 2.36 (t, J=7.3 Hz, 2H), 2.00-1.88 (m, 2H). From the NMR data, Form CSIV has no solvent residue.

TABLE 13

| Diffraction angle 2θ (°) | d spacing (Å) | Relative intensity (%) |
|---|---|---|
| 7.33 | 12.06 | 5.85 |
| 8.90 | 9.93 | 21.90 |
| 9.38 | 9.43 | 11.22 |
| 11.39 | 7.77 | 43.59 |
| 11.70 | 7.56 | 20.29 |
| 14.36 | 6.17 | 14.62 |
| 14.73 | 6.01 | 10.75 |
| 15.31 | 5.79 | 36.30 |
| 15.94 | 5.56 | 31.84 |
| 16.98 | 5.22 | 30.27 |
| 17.17 | 5.17 | 41.22 |
| 17.52 | 5.06 | 32.75 |
| 17.85 | 4.97 | 53.87 |
| 18.11 | 4.90 | 21.88 |
| 18.84 | 4.71 | 17.91 |
| 19.51 | 4.55 | 8.14 |
| 20.07 | 4.42 | 31.20 |
| 20.94 | 4.24 | 32.20 |
| 22.21 | 4.00 | 26.50 |
| 22.89 | 3.89 | 13.41 |
| 23.63 | 3.77 | 9.05 |
| 24.32 | 3.66 | 46.19 |
| 24.66 | 3.61 | 100.00 |
| 25.78 | 3.46 | 70.90 |
| 27.62 | 3.23 | 53.41 |
| 29.01 | 3.08 | 16.25 |
| 30.73 | 2.91 | 10.33 |
| 31.76 | 2.82 | 7.05 |
| 34.39 | 2.61 | 1.92 |
| 36.73 | 2.45 | 3.11 |
| 38.65 | 2.33 | 3.50 |

Example 8 Repeat the Preparation Method of Compound I Disclosed in the Prior Art According to Table 14, a certain amount of Compound I solid was dissolved by a certain volume of ethyl acetate to dissolve the solid. The solution was filtered. A certain volume of the filtrate was concentrated under reduced pressure at a certain temperature to obtain a solid. The obtained solid was labeled as Samples 1-2.

TABLE 14

| Sample | Weight of Compound I (mg) | Ethyl acetate volume (mL) | Filtrate volume (mL) | Temperature of concentration (° C.) | Vcuum drying under 30° C. | Sample appearance | Solid form |
|---|---|---|---|---|---|---|---|
| 1 | 250.1 | 80 | 30 | 40 | Yes | flocculent powder | amorphous |
| 2 | 250.1 | 80 | 16 | 40 | No | transparent gelatinous solid | amorphous |

Samples 1-2 were confirmed by XRPD to be amorphous.

Figure 11:
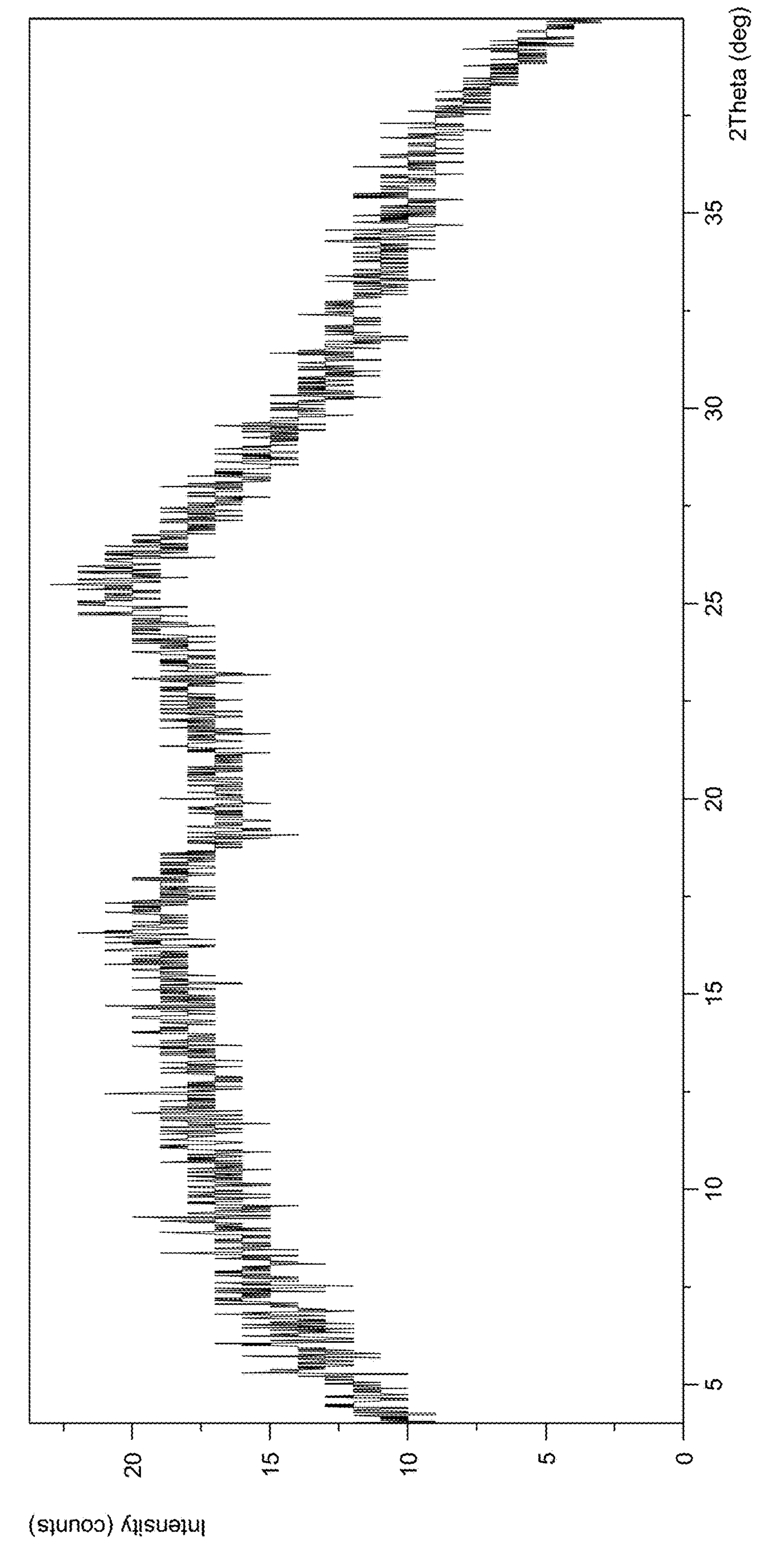
FIG. 11 shows an XRPD pattern of amorphous according to example 8.

The XRPD pattern of Sample 1 is substantially as depicted in FIG. 11.

Figure 12:
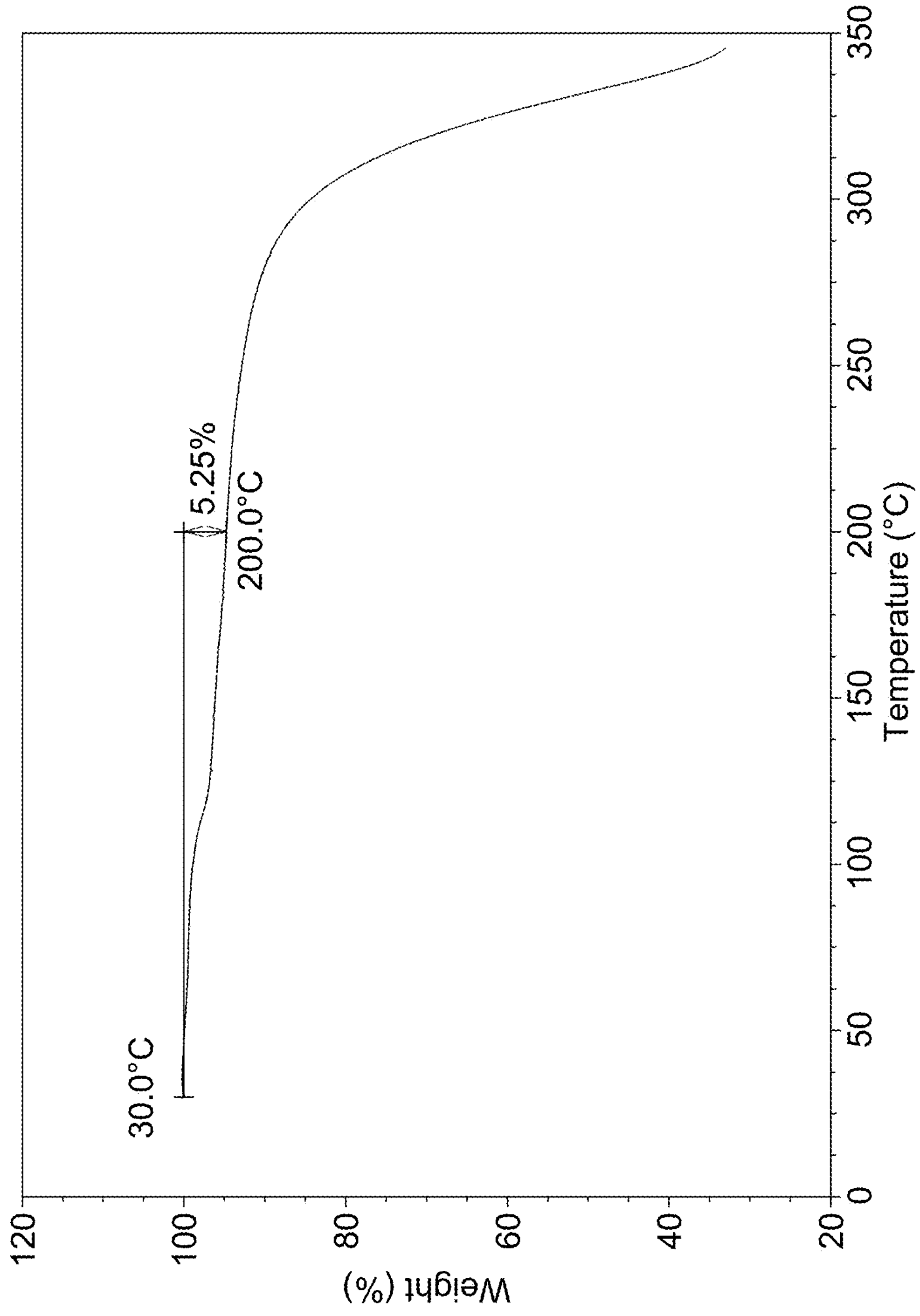
FIG. 12 shows a TGA curve of amorphous according to example 8.

The TGA curve of Sample 1 is substantially as depicted in FIG. 12, which shows about 5.3% weight loss when heated to 200° C.

The $^1H$ NMR data of Sample 1 are: $^1H$ NMR (400 MHz, DMSO-d6) δ(ppm) 12.11 (s, 1H), 9.65 (s, 1H), 8.97 (d, J=2.0 Hz, 1H), 8.20 (d, J=8.8 Hz, 1H), 8.09 (d, J=8.9 Hz, 1H), 7.84 (dd, J=8.7, 2.1 Hz, 1H), 7.57 (d, J=2.1 Hz, 1H), 7.31 (dd, J=8.9, 2.3 Hz, 1H), 6.61 (s, 1H), 3.08 (t, J=14.8 Hz, 1H), 2.36 (t, J=7.3 Hz, 2H), 1.97-1.90 (m, 2H). The NMR signals at (δ(ppm) 4.03 (q, J=7.1 Hz), 1.17 (t, J=7.1 Hz, 0.58H)) belong to ethyl acetate. NMR results show that the prior art amorphous contains 2.70 wt % of ethyl acetate.

Example 9 Physical and Chemical Stability of Form CSI

Figure 13:
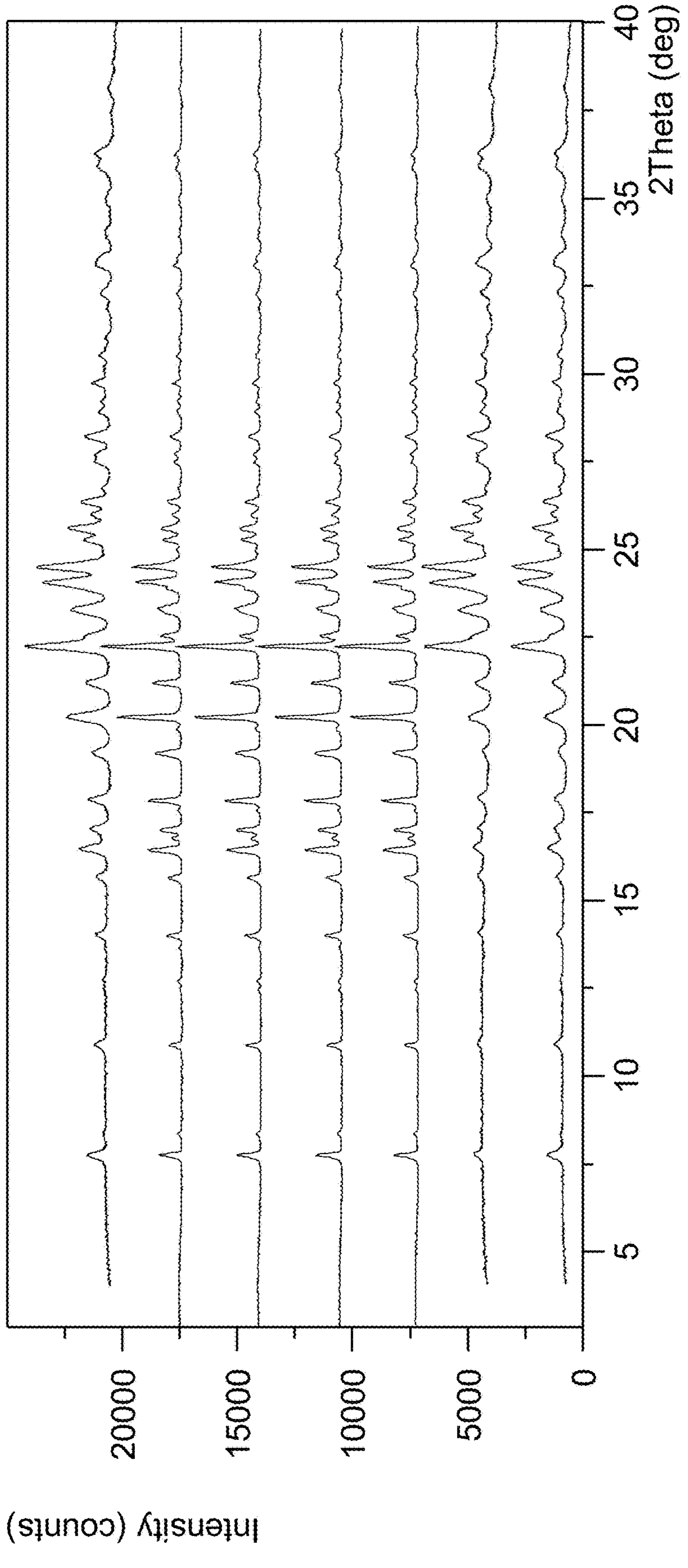
FIG. 13 shows an XRPD pattern overlay of Form CSI before and after storage under different conditions (from top to bottom: initial, 25° C./60% RH for 6 months with open package, 25° C./60% RH for 6 months with sealed package, 40° C./75% RH for 6 months with open package, 40° C./75% RH for 6 months with sealed package, 60° C./75% RH for 3 months with open package, 60° C./75% RH for 3 months with sealed package.)

A certain amount of Form CSI of the present disclosure was stored under different conditions of 25° C./60% RH, 40° C./75% RH, and 60° C./75% RH. Crystalline form and chemical purity were checked by XRPD and HPLC, respectively. The results are shown in Table 15, and the XRPD overlay is shown in FIG. 13.

TABLE 15

| Initial | Conditions | Packing conditions | Time | Purity change | Form |
|---|---|---|---|---|---|
| CSI | Initial | N/A | — | N/A | Form CSI |
| | 25° C./60% RH | Sealed packaged | 6 months | 0.03% | Form CSI |
| | 25° C./60% RH | Open packaged | 6 months | 0.02% | Form CSI |
| | 40° C./75% RH | Sealed packaged | 6 months | 0.01% | Form CSI |
| | 40° C./75% RH | Open packaged | 6 months | 0.05% | Form CSI |
| | 60° C./75% RH | Sealed packaged | 3 months | 0.07% | Form CSI |
| | 60° C./75% RH | Open packaged | 3 months | 0.08% | Form CSI |

Open packaged: Put the sample into a glass vial, cover the vial with aluminum toil, and punch 5-10 holes in the foil.

Sealed packaged: Put the sample into a glass vial, cap the vial tightly, and seal the vial in an aluminum foil bag.

The results show that Form CSI is stable for at least 6 months under 25° C./60% RH and 40° C./75% RH. It shows that Form CSI has good stability under long-term and accelerated conditions. Form CSI is stable for at least 3 months under 60° C./75% RH. It shows that Form CSI has good stability under more stress conditions.

Example 10 Hygroscopicity of Amorphous

Dynamic vapor sorption (DVS) analyzer was applied to evaluate the hygroscopicity of amorphous with a certain amount of sample. The weight gains at each relative humidity were recorded in a cycle of 0-95% RH-0. The results show that the weight gains of amorphous from 0 to 60% RH and from 0 to70% RH are 0.94% and 1.18%.

Example 11 Hygroscopicity of Form CSI

Dynamic vapor sorption (DVS) analyzer was applied to evaluate hygroscopicity of Form CSI with a certain amount of sample. The weight gains at each relative humidity were recorded in a cycle of 0-95% RH-0.

Figure 14:
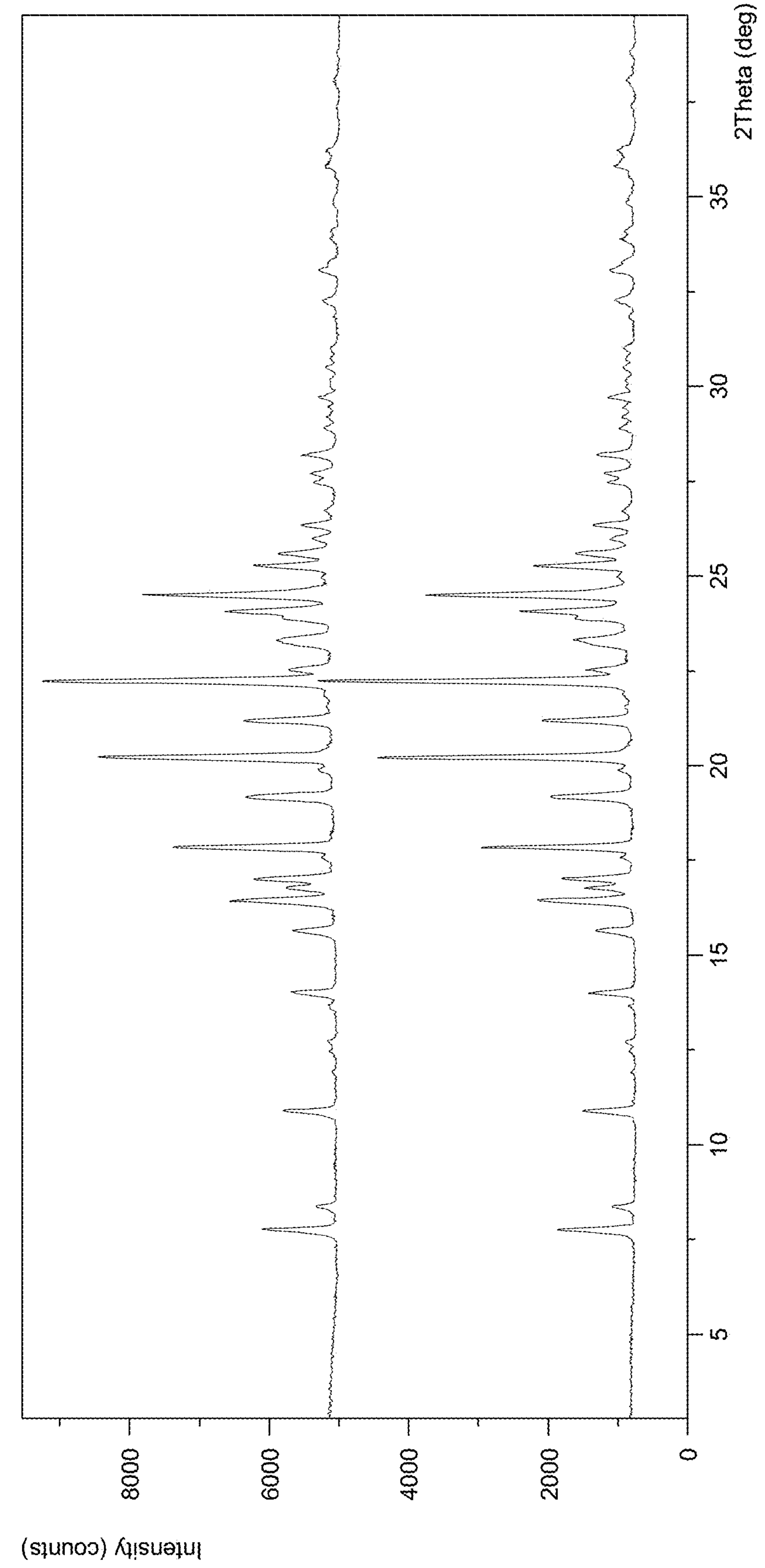
FIG. 14 shows an XRPD pattern overlay of Form CSI before and after DVS test (top: before testing, bottom: after testing)

The results show that the weight gains of Form CSI from 0 to 60% RH and from 0 to 70% RH are both 0.17%. The weight gains of amorphous from 0 to 60% RH and from 0 to 70% RH are about 6 times and 7 times that of Form CSI. The XRPD patterns of Form CSI before and after DVS are shown in FIG. 14, and the crystalline state of Form CSI remains unchanged after DVS.

Example 12 Appearance of Form CSI

Figure 15:
FIG. 15 shows the appearance of Form CSI powder.

A certain amount of Form CSI was weighed and put on sulphuric acid paper to observe the appearance The appearance of Form CSI is shown in FIG. 15. The result shows that Form CSI is powdery with uniformly dispersed and has no adhesion phenomenon.

Example 13 Particle Size Distribution of Form CSI

A certain amount of Form CSI was added into a glass vial with about a certain volume of Isopar G (containing 0.2% lecithin). The mixture was mixed thoroughly and transferred into the Hydro MV dispersing device. The experiment was started when the obscuration was in appropriate range. The particle size distribution was tested after 30 seconds of ultrasonication. The results are shown in Table 16.

TABLE 16

| Form | MV (μm) | D10 (μm) | D50 (μm) | D90 (μm) |
|---|---|---|---|---|
| Form CSI | 4.54 | 0.725 | 1.89 | 7.15 |

The results show that the particle size of Form CSI is small and uniform.

Example 14 Flowability of Form CSI

Compressibility index is usually utilized to evaluate the flowability of powder or granules during the drug product process. Compressibility index test method is as follows: a certain amount of powder was added into a measuring cylinder and bulk volume was recorded. Then the powder was tapped to make it in the tightest state and the tapped volume was recorded. The bulk density ($\rho_0$) and tapped density (ρf) were calculated and compressibility index was calculated according to $c=(\rho f-\rho_0)/\rho f$.

Criteria of flowability according to ICH Q4B Annex 13 is shown in Table 17.

TABLE 17

| Compressibility index (%) | Flowability |
|---|---|
| ≤10 | Excellent |
| 11-15 | Good |
| 16-20 | Fair |
| 21-25 | Passable |
| 26-31 | Poor |
| 32-37 | Very poor |
| >38 | Very, very poor |

Flowability test results of Form CSI is presented in Table 18, which indicate that Form CSI has good flowability.

TABLE 18

| Form | Bulk density (g/mL) | Tapped density (g/mL) | Flowability |
|---|---|---|---|
| CSI | 0.405 | 0.526 | Passable |

Example 15 Adhesiveness of Form CSI

ENERPAC manual tablet press was used for testing. Approximately 30 mg of Form CSI was weighed and then added into the dies of φ8 mm round tooling, compressed at 10 kN and held for 30 s. The punch was weighed and the amount of material sticking to the punch was calculated. The compression was repeated twice and the maximum amount and average amount of material sticking to the punch during the compression were recorded. The results show that the average adhesion amount of Form CSI was 0.45 mg.

Example 16 Physical and Chemical Stability of Form CSII

Figure 16:
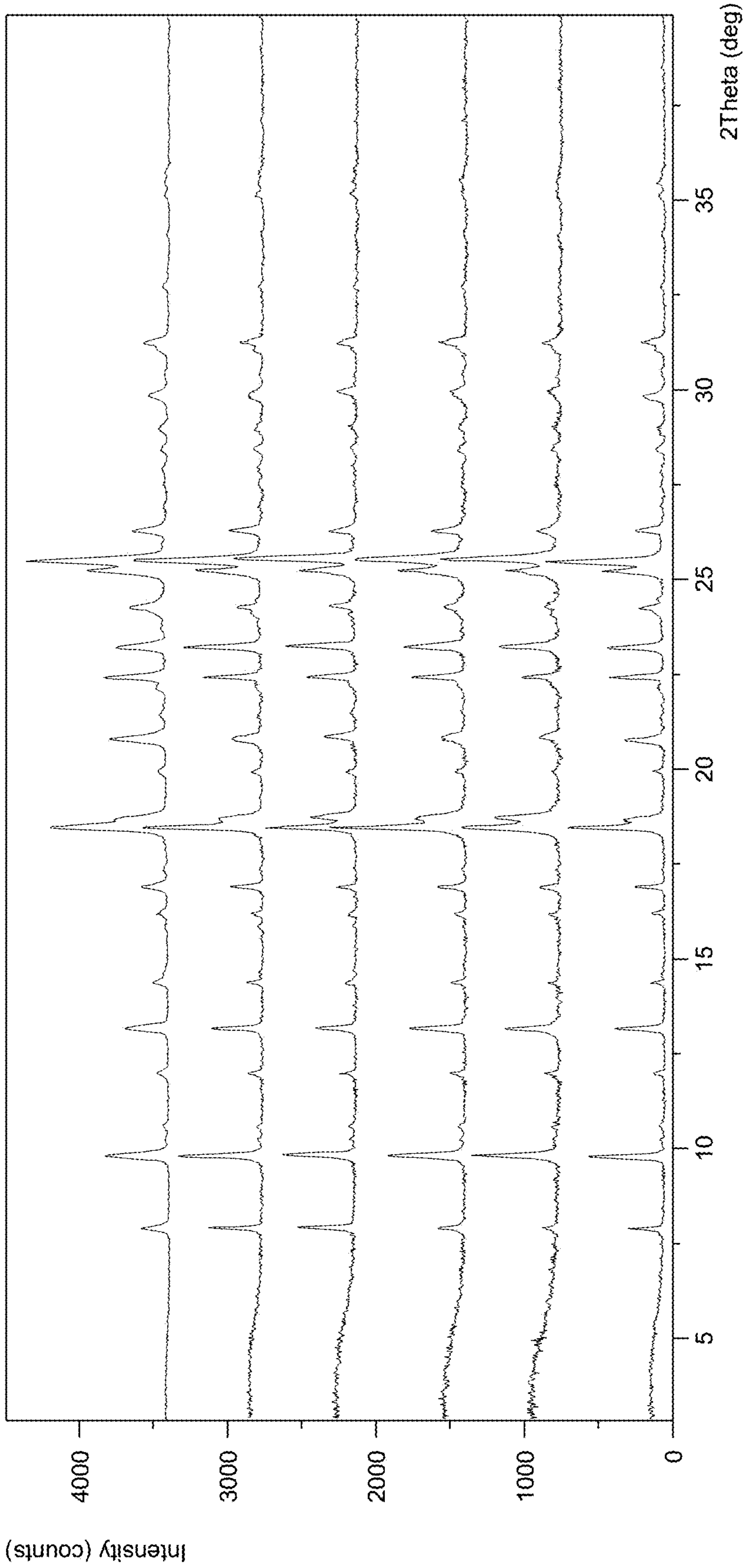
FIG. 16 shows an XRPD pattern overlay of Form CSII before and after storage with different conditions (from top to bottom: initial, 25° C./60% RH for 3 months with open packaged, 25° C./60% RH for 3 months with sealed packaged, 40° C./75% RH for 3 months with open packaged, 40° C./75% RH for 3 months with sealed packaged, 60° C./75% RH for one month with open packaged.)

A certain amount of Form CSII of the present disclosure was stored under different conditions of 25° C./60% RH, 40° C./75% RH, and 60° C./75% RH. Crystalline form and chemical purity were checked by XRPD and HPLC, respectively. The results are shown in Table 19, and the XRPD overlay is shown in FIG. 16.

TABLE 19

| Initial Conditions | | Packing conditions | Time | Purity change | Form |
|---|---|---|---|---|---|
| CSII | Initial | N/A | — | N/A | Form CSII |
| | 25° C./60% RH | Sealed packaged | 3 months | 0.06% | Form CSII |
| | 25° C./60% RH | Open packaged | 3 months | 0.09% | Form CSII |
| | 40° C./75% RH | Sealed packaged | 3 months | 0.01% | Form CSII |
| | 40° C./75% RH | Open packaged | 3 months | 0.07% | Form CSII |
| | 60° C./75% RH | Open packaged | one month | 0.05% | Form CSII |

Open packaged: Put the sample into a glass vial, cover the vial with aluminum foil, and punch 5-10 holes in the foil.

Sealed packaged: Put the sample into a glass vial, cap the vial tightly, and seal the vial in an aluminum foil bag.

The results show that Form CSII is stable for at least 3 months under 25° C./60% RH and 40° C./75% RH. It shows that Form CSII has good stability under long-term and accelerated conditions. Form CSII is stable for at least one month under 60° C./75% RH. It shows that Form CSII has good stability under more stress conditions.

Example 17 Physical Stability of Form CSII Upon Mechanical Force

Figure 17:
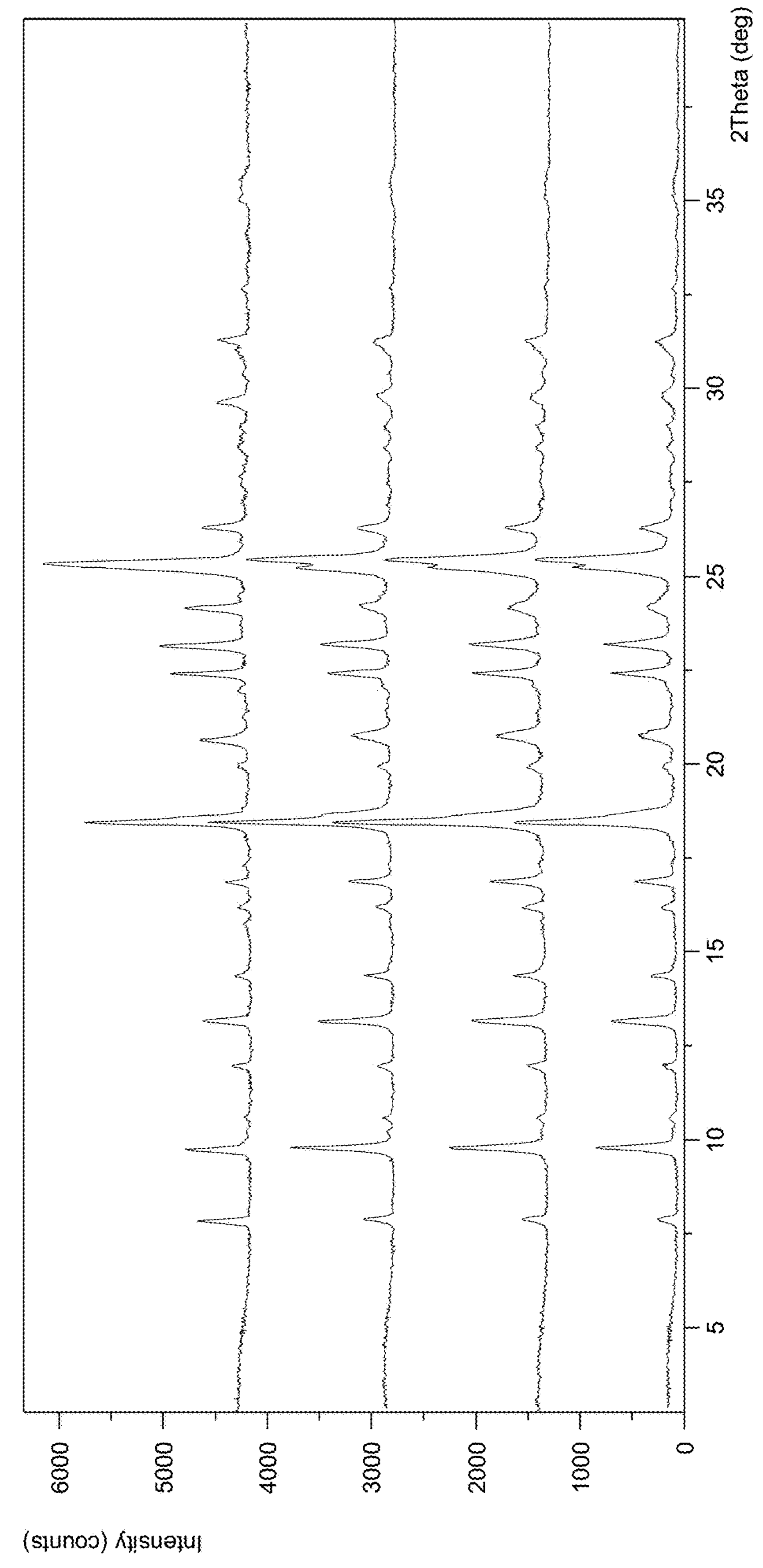
FIG. 17 shows an XRPD pattern overlay of Form CSII before and after tableting (from top to bottom: initial, 5 kN, 10 kN, 20 kN).

A certain amount of Form CSII was compressed into tablet under different pressures with suitable tableting die. Crystalline form before and after tableting were checked by XRPD. The test results are shown in Table 20, the XRPD pattern before and after tableting are shown in FIG. 17. The results show that Form CSII has good stability under different pressures.

TABLE 20

| Before tableting | Pressure | Solid form after tableting |
|---|---|---|
| Form CSII | 5 kN | Form CSII |
| | 10 kN | Form CSII |
| | 20 kN | Form CSII |

Figure 18:
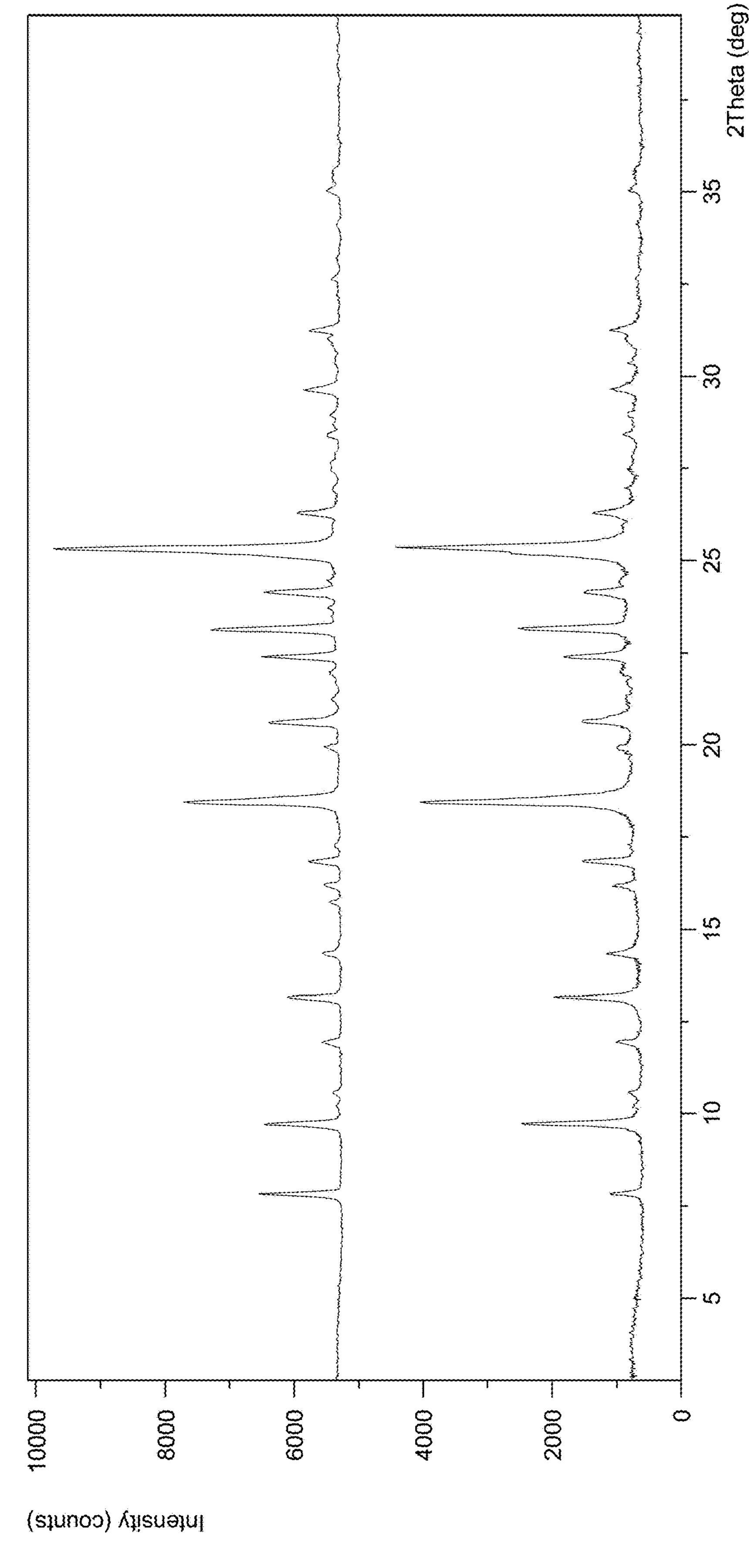
FIG. 18 shows an XRPD pattern overlay of Form CSII before and after grinding (top: before grinding; bottom: after grinding).

Form CSII was grounded manually for 5 minutes in a mortar. The XRPD patterns overlay before and after grinding is shown in FIG. 18. The results show that the crystalline state Form CSII remains unchanged after grinding.

Example 18 Hygroscopicity of Form CSII

Dynamic vapor sorption (DVS) analyzer was applied to evaluate hygroscopicity of Form CSII with a certain amount of sample. The weight gains at each relative humidity were recorded in a cycle of 50% RH-95% RH-0%-95% RH.

Figure 19:
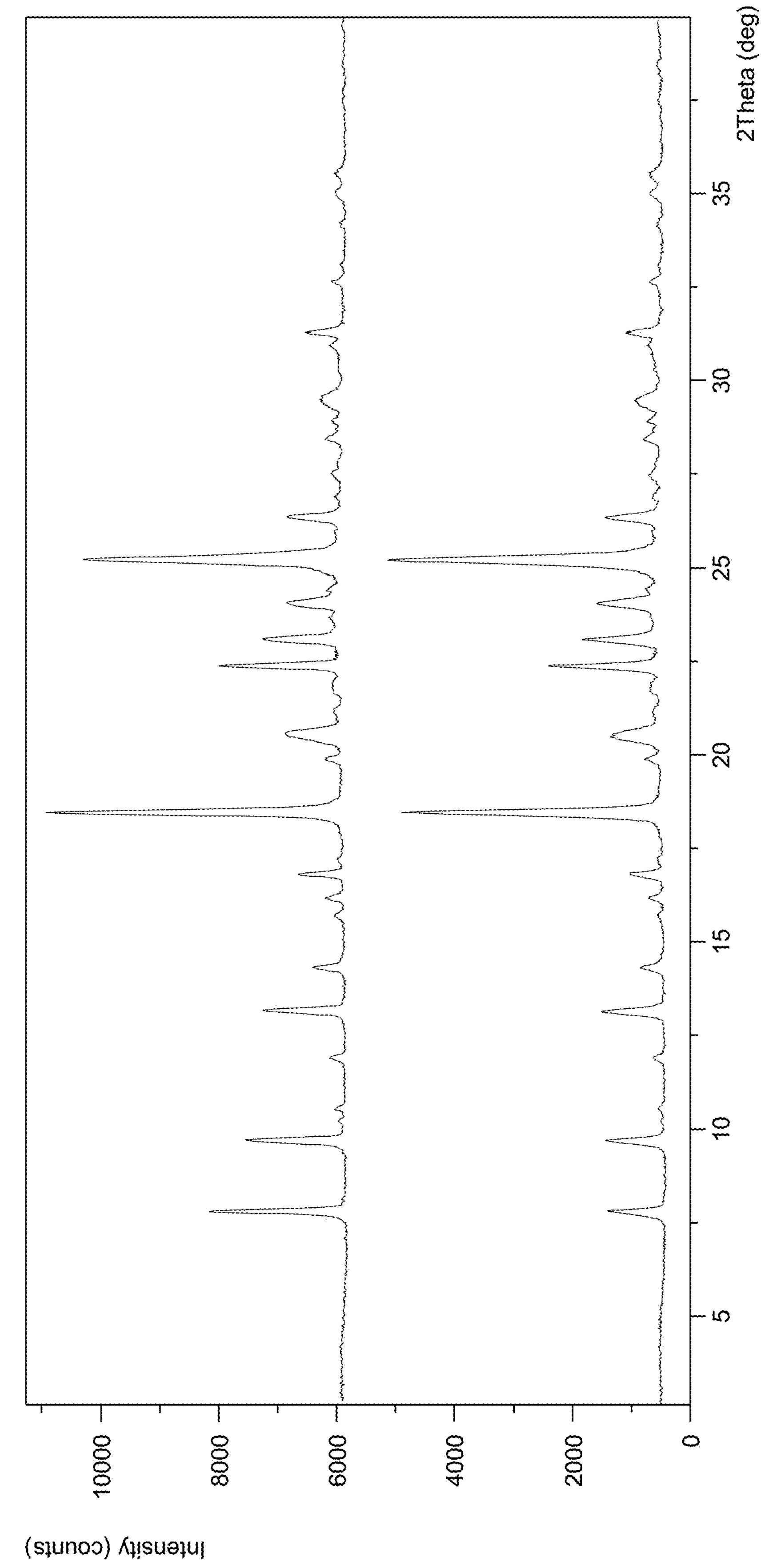
FIG. 19 shows an XRPD pattern overlay of Form CSII before and after DVS test (top: before testing, bottom: after testing).

The results show that the weight gains of Form CSII from 0 to 60% RH and from 0 to 70% RH are 0.21% and 0.27%. The weight gains of amorphous are about 4 times and 5 times that of Form CSII. The XRPD patterns of Form CSII before and after DVS are shown in FIG. 19, and the crystalline state of Form CSII remains unchanged after DVS.

Example 19 Appearance of Form CSII

Figure 20:
FIG. 20 shows the appearance of Form CSII powder.

A certain amount of Form CSII was weighed and put in sulphuric acid paper, and the powder state was observed. The appearance of Form CSII is shown in FIG. 20. The result shows that Form CSII is powdery with uniformly dispersed and has no adhesion phenomenon.

Example 20 Adhesiveness of Form CSII

ENERPAC manual tablet press was used for testing. Approximately 30 mg of Form CSII was weighed and then added into the dies of φ8 mm round tooling, compressed at 10 kN and held for 30 s. The punch was weighed and amount of material sticking to the punch was calculated. The compression was repeated twice and the maximum amount and average amount of material sticking to the punch during the compression were recorded. The results show that the average adhesion amount of Form CSII was 0.20 mg.

Example 21 Physical and Chemical Stability of Form CSIV

Figure 21:
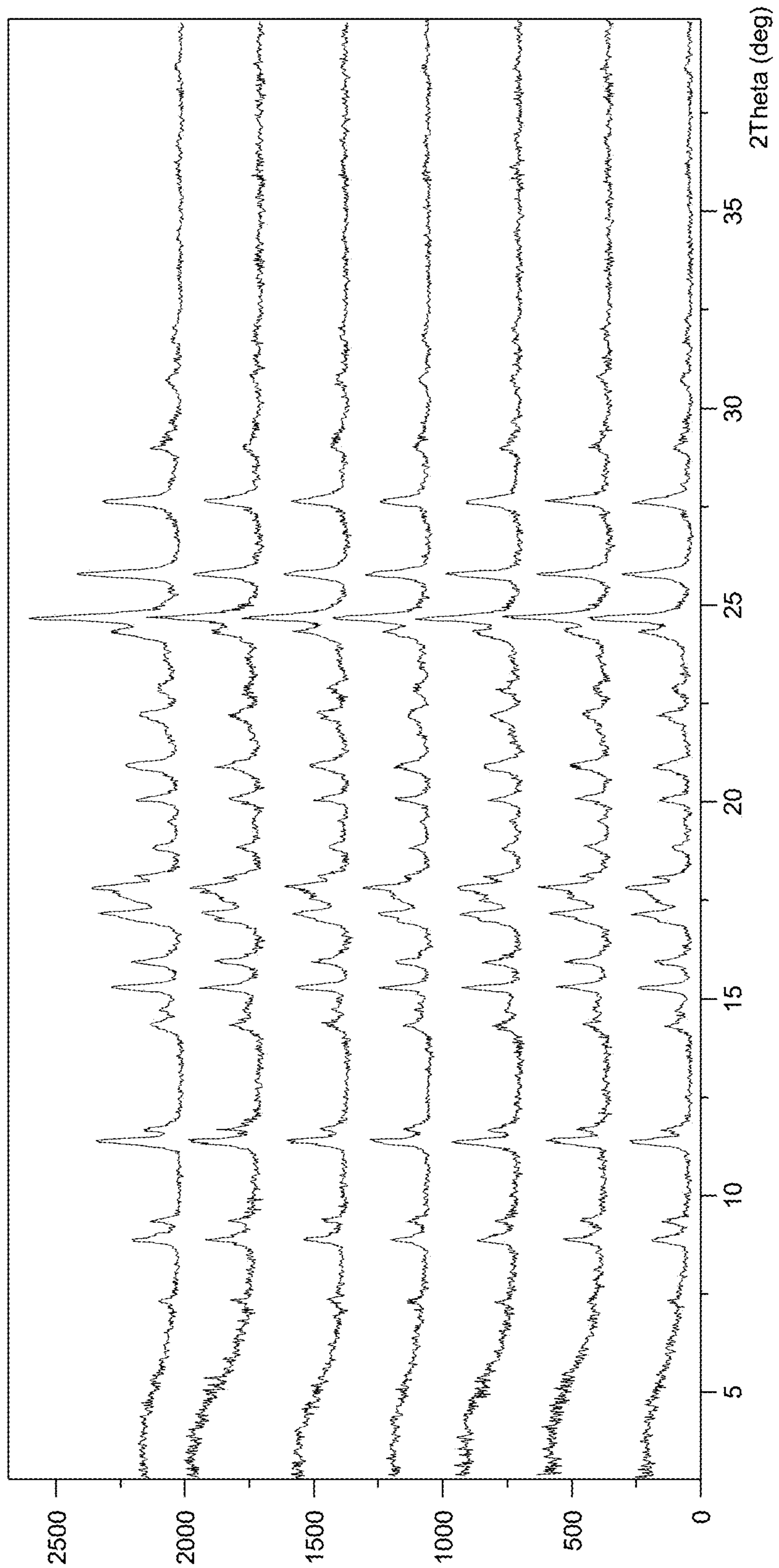
FIG. 21 shows an XRPD pattern overlay of Form CSIV before and after storage with different conditions (from top to bottom: initial, 25° C./60% RH for 3 months with open package, 25° C./60% RH for 3 months with sealed package, 40° C./75% RH for 3 months with open package, 40° C./75% RH for 3 months with sealed package, 60° C./75% RH for one month with open package, 60° C./75% RH for one month with sealed package.)

A certain amount of Form CSIV of the present disclosure was stored under different conditions of 25° C./60% RH, 40° C./75% RH, and 60° C./75% RH. Crystalline form and chemical purity were checked by XRPD and HPLC, respectively. The results are shown in Table 21, and the XRPD overlay is shown in FIG. 21.

TABLE 21

| Initial Conditions | | Packing conditions | Time | Purity change | Form |
|---|---|---|---|---|---|
| CSIV | Initial | N/A | — | N/A | Form CSIV |
| | 25° C./60% RH | Sealed packaged | 3 months | 0.04% | Form CSIV |
| | 25° C./60% RH | Open packaged | 3 months | 0.02% | Form CSIV |
| | 40° C./75% RH | Sealed packaged | 3 months | 0.03% | Form CSIV |

TABLE 21-continued

| Initial Conditions | Packing conditions | Time | Purity change | Form |
|---|---|---|---|---|
| 40° C./75% RH | Open packaged | 3 months | 0.00% | Form CSIV |
| 60° C./75% RH | Sealed packaged | one month | 0.06% | Form CSIV |
| 60° C./75% RH | Open packaged | one month | 0.04% | Form CSIV |

Open packaged: Put the sample into a glass vial, cover the vial with aluminum foil, and punch 5-10 holes in the foil.

Sealed packaged: Put the sample into a glass vial, cap the vial tightly, and seal the vial in an aluminum foil bag.

The results show that Form CSIV is stable for at least 3 months under 25° C./60% RH and 40° C./75% RH. It shows that Form CSIV has good stability under long-term and accelerated conditions. Form CSIV is stable for at least one month under 60° C./75% RH. It shows that Form CSIV has good stability under more stress conditions.

Example 22 Physical Stability of Form CSIV Upon Mechanical Force

Figure 22:
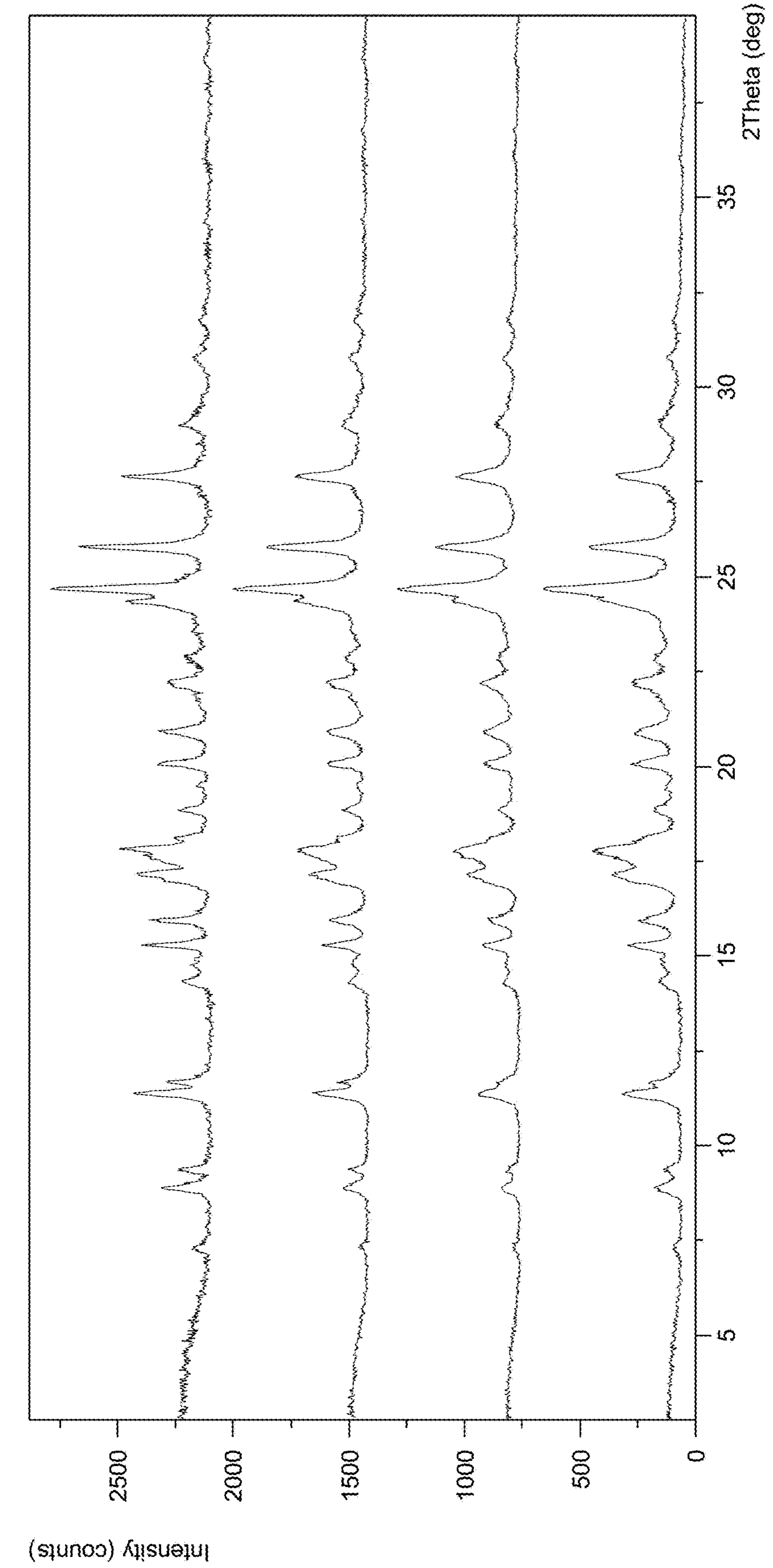
FIG. 22 shows an XRPD pattern overlay of Form CSIV before and after tableting (from top to bottom: initial, 5 kN, 10 kN, 20 kN).

A certain amount of Form CSIV was compressed into tablet under different pressures with suitable tableting die. Crystalline form before and after tableting were checked by XRPD. The test results are shown in Table 22, the XRPD pattern before and after tableting are shown in FIG. 22. The results show that Form CSIV has good stability under different pressures.

TABLE 22

| Before tableting | Pressure | Solid form after tableting |
|---|---|---|
| Form CSIV | 5 kN | Form CSIV |
| | 10 kN | Form CSIV |
| | 20 kN | Form CSIV |

Figure 23:
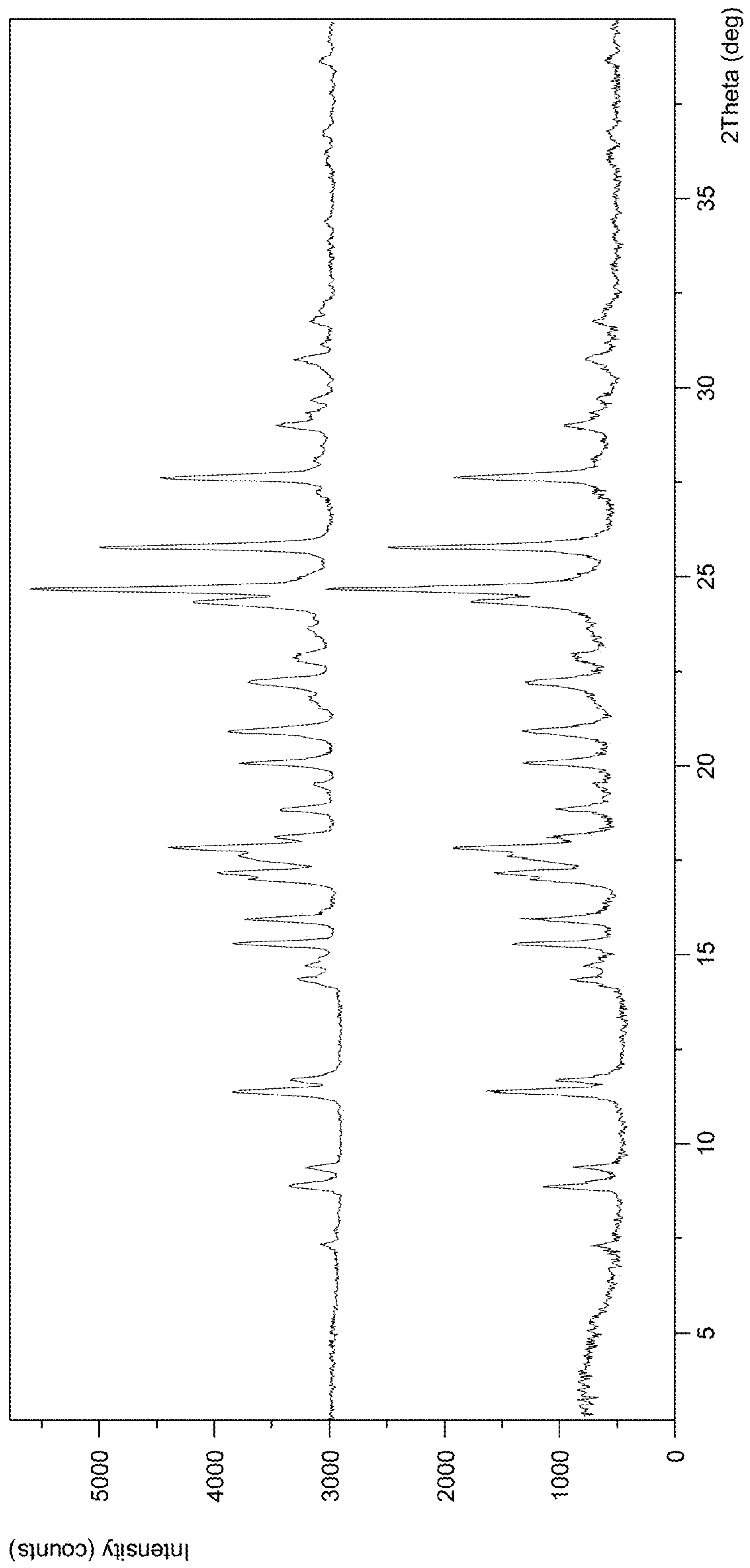
FIG. 23 shows XRPD pattern overlay of Form CSIV before and after grinding (top: before grinding; bottom: after grinding).

Form CSIV was grounded manually for 5 minutes in a mortar. The XRPD patterns overlay before and after grinding is shown in FIG. 23. The results show that the crystalline state Form CSIV remains unchanged after grinding, which has good physical stability.

Example 23 Hygroscopicity of Form CSIV

Dynamic vapor sorption (DVS) analyzer was applied to evaluate hygroscopicity of Form CSIV and prior art amorphous with certain amounts of samples. The weight gains at each relative humidity were recorded in a cycle of 0-95% RH-0.

Figure 24:
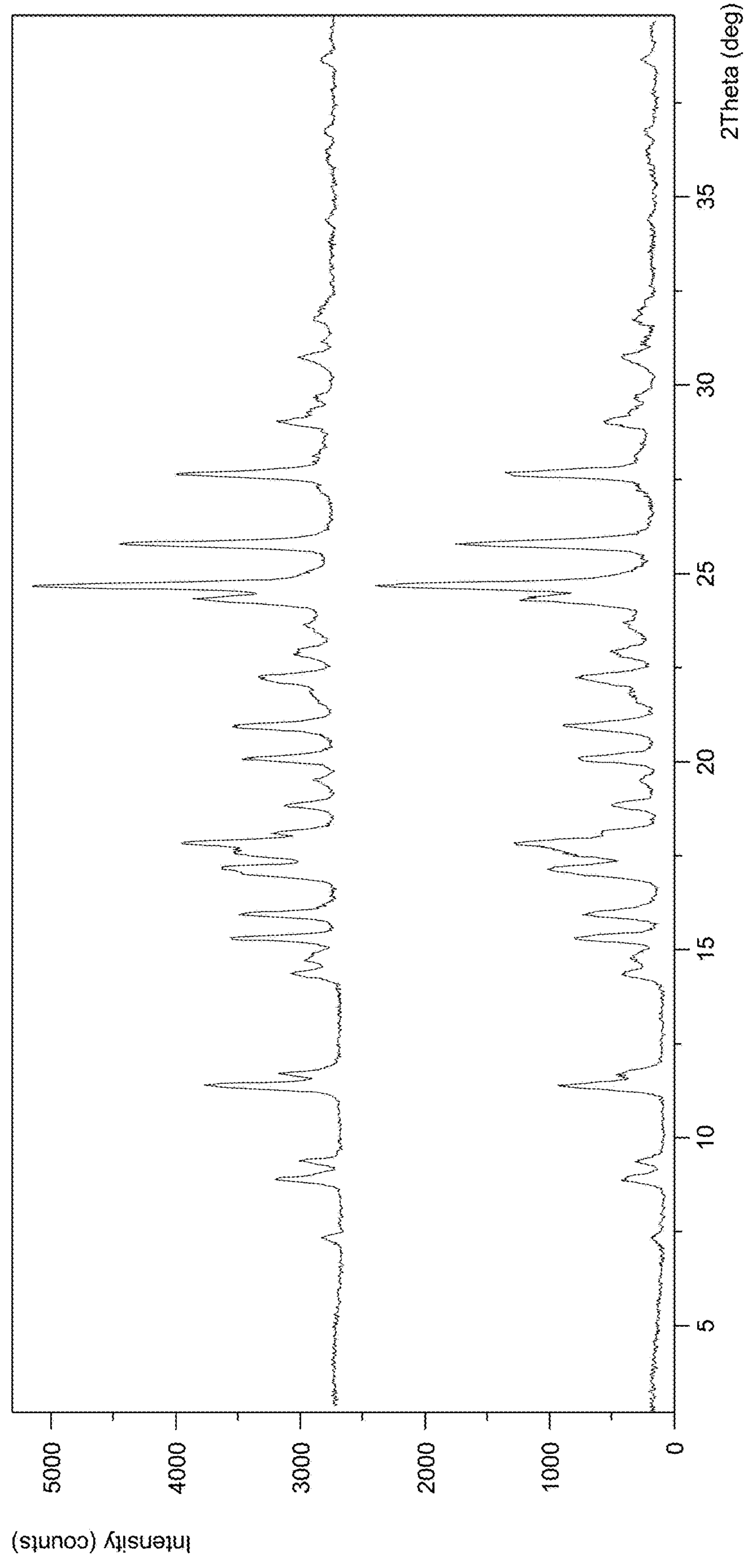
FIG. 24 shows an XRPD pattern overlay of Form CSIV before and after DVS test (top: before testing, bottom: after testing).

The results show that the weight gain of Form CSIV under 0-60% RH and 0-70% RH are 0.23% and 0.27%. The weight gain of amorphous are about 4 times that of Form CSIV. The XRPD patterns of Form CSIV before and after DVS are shown in FIG. 24, and the crystalline state of Form CSIV remains unchanged after DVS.

Example 24 Appearance of Form CSIV

Figure 25:
FIG. 25 shows the appearance of Form CSIV powder.

A certain amount of Form CSIV was weighed and put in sulphuric acid paper, and the powder state was observed. The appearance of Form CSIV is shown in FIG. 25. The result shows that Form CSIV is powdery with uniformly dispersed and has no adhesion phenomenon.

Example 25 Adhesiveness of Form CSIV

ENERPAC manual tablet press was used for testing. Approximately 30 mg of Form CSIV was weighed and then added into the dies of φ8 mm round tooling, compressed at 10 KN and held for 30 s. The punch was weighed and amount of material sticking to the punch was calculated. The compression was repeated twice and the maximum amount and average amount of material sticking to the punch during the compression were recorded. The results show that the average adhesion amount of Form CSIV was 0.05 mg.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A crystalline form of Compound I, wherein the X-ray powder diffraction pattern comprises characteristic peaks at 2theta values of 18.4°±0.2°, 22.4°±0.2° and 25.3°±0.2° using CuKα radiation, Compound I

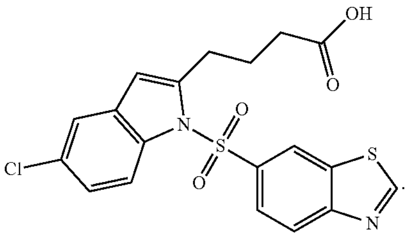

.

2. The crystalline form of Compound I according to claim 1, wherein the X-ray powder diffraction pattern comprises at least one characteristic peaks at 2theta values of 7.9°±0.2°, 13.2°±0.2° and 20.6°±0.2° using CuKα radiation.

3. The crystalline form of Compound I according to claim 1, wherein the X-ray powder diffraction pattern comprises at least one characteristic peaks at 2theta values of 9.7°±0.2°, 23.1°±0.2° and 24.2°±0.2° using CuKα radiation.

4. The crystalline form of Compound I according to claim 2, wherein the X-ray powder diffraction pattern comprises at least one characteristic peaks at 2theta values of 9.7°±0.2°, 23.1°±0.2° and 24.2°±0.2° using CuKα radiation.

5. The crystalline form of Compound I according to claim 1, wherein the X-ray powder diffraction pattern is substantially as depicted in FIG. 5 using CuKα radiation.

6. A crystalline form of Compound I, wherein the X-ray powder diffraction pattern comprises characteristic peaks at 2theta values of 11.4°±0.2°, 24.7°±0.2° and 25.8°±0.2° using CuKα radiation, Compound I

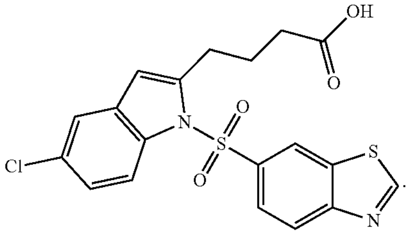

7. The crystalline form of Compound I according to claim 6, wherein the X-ray powder diffraction pattern comprises at least one characteristic peaks at 2theta values of 15.3°±0.2°, 20.1°±0.2° and 27.6°±0.2° using CuKα radiation.

8. The crystalline form of Compound I according to claim 6, wherein the X-ray powder diffraction pattern comprises at least one characteristic peaks at 2theta values of 8.9°±0.2°, 15.9°±0.2°, and 20.9°±0.2° using CuKα radiation.

9. The crystalline form of Compound I according to claim 7, wherein the X-ray powder diffraction pattern comprises at least one characteristic peaks at 2theta values of 8.9°±0.2°, 15.9°±0.2°, and 20.9°±0.2° using CuKα radiation.

10. The crystalline form of Compound I according to claim 6, wherein the X-ray powder diffraction pattern is substantially as depicted in FIG. 9 using CuKα radiation.

11. A pharmaceutical composition, wherein said pharmaceutical composition comprises a therapeutically effective amount of crystalline form of Compound I according to claim 1, and pharmaceutically acceptable excipients.

12. A pharmaceutical composition, wherein said pharmaceutical composition comprises a therapeutically effective amount of crystalline form of Compound I according to claim 6, and pharmaceutically acceptable excipients.

* * * * *